United States Patent
Goetz

(10) Patent No.: US 9,180,303 B2
(45) Date of Patent: Nov. 10, 2015

(54) TRANSMISSION OF POWER SOURCE USAGE INFORMATION OVER A NETWORK

(75) Inventor: Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 1021 days.

(21) Appl. No.: 12/738,026

(22) PCT Filed: Sep. 29, 2008

(86) PCT No.: PCT/US2008/078114
§ 371 (c)(1),
(2), (4) Date: Apr. 14, 2010

(87) PCT Pub. No.: WO2009/055204
PCT Pub. Date: Apr. 30, 2009

(65) Prior Publication Data
US 2010/0222847 A1    Sep. 2, 2010

Related U.S. Application Data

(60) Provisional application No. 61/000,159, filed on Oct. 24, 2007.

(51) Int. Cl.
*A61N 1/378* (2006.01)
*A61N 1/372* (2006.01)
(Continued)

(52) U.S. Cl.
CPC ....... *A61N 1/37252* (2013.01); *A61M 5/14276* (2013.01); *G06F 19/3412* (2013.01);
(Continued)

(58) Field of Classification Search
CPC ............ A61N 1/37252; A61N 1/3975; A61N 1/3787; A61N 1/37276; A61N 1/37282

USPC .................................. 607/29, 32–33, 60–61
See application file for complete search history.

(56) References Cited

U.S. PATENT DOCUMENTS 6,044,297 A    3/2000  Sheldon et al.
6,662,052 B1  12/2003  Sarwal et al.
(Continued)

FOREIGN PATENT DOCUMENTS

EP    1491234    12/2004
WO    WO96/22125    7/1996
(Continued)

OTHER PUBLICATIONS

PCT/US08/78134; Search Report and Written Opinion dated Jun. 9, 2009.
(Continued)

*Primary Examiner* — Michael Kahelin
*Assistant Examiner* — Minh Duc Pham
(74) *Attorney, Agent, or Firm* — Shumaker & Sieffert, P.A.

(57) ABSTRACT

The disclosure is directed to transmitting power source usage information regarding a power source of an implantable medical device (IMD) to a remote networking device via a network. The IMD operates on power supplied by a power source, such as a battery, within the housing of the IMD. The use of the power source may be monitored remotely in order to maintain therapy. Power source usage information may include power source recharge patterns such as frequency of recharging events, length of recharging events, period between recharging events, discharge state of the power source, and degree of coupling between primary and secondary coils during recharging. The IMD, or an external device used with the IMD, may generate, store, and transmit the power source usage information to the remote networking device. Action requests may be transmitted from the remote networking device via the network based upon the power source usage information.

27 Claims, 14 Drawing Sheets

(51) Int. Cl.
*A61M 5/142* (2006.01)
*G06F 19/00* (2011.01)
*A61B 5/00* (2006.01)

(52) U.S. Cl.
CPC ....... *A61B5/0002* (2013.01); *A61B 2560/0209* (2013.01); *A61M 2205/3523* (2013.01); *A61M 2205/3553* (2013.01); *A61M 2205/3584* (2013.01); *A61M 2205/8212* (2013.01); *A61M 2205/8243* (2013.01); *A61N 1/37282* (2013.01)

(56) References Cited

U.S. PATENT DOCUMENTS

| | | | |
|---|---|---|---|
| 2001/0031997 | A1 | 10/2001 | Lee |
| 2002/0029002 | A1 | 3/2002 | Bardy |
| 2002/0052539 | A1* | 5/2002 | Haller et al. ............... 600/300 |
| 2002/0143372 | A1 | 10/2002 | Snell et al. |
| 2002/0183693 | A1 | 12/2002 | Peterson et al. |
| 2003/0114899 | A1* | 6/2003 | Woods et al. ............... 607/60 |
| 2004/0073264 | A1* | 4/2004 | Lyden ............... 607/7 |
| 2005/0277994 | A1* | 12/2005 | McNamee et al. ............ 607/29 |
| 2006/0089592 | A1 | 4/2006 | Kadhiresan et al. |
| 2006/0235289 | A1 | 10/2006 | Wesselink |
| 2007/0142868 | A1 | 6/2007 | Moon et al. |
| 2007/0150019 | A1* | 6/2007 | Youker et al. ............ 607/29 |
| 2008/0221644 | A1* | 9/2008 | Vallapureddy et al. ....... 607/60 |

FOREIGN PATENT DOCUMENTS

| | | |
|---|---|---|
| WO | WO2004/067083 | 8/2004 |
| WO | WO2004/093989 | 11/2004 |
| WO | WO2006/099035 | 9/2006 |
| WO | WO2007/079543 | 7/2007 |
| WO | WO2007/112092 | 10/2007 |
| WO | WO2009/055202 | 4/2009 |
| WO | WO2009/055204 | 4/2009 |
| WO | WO2009/055205 | 4/2009 |
| WO | WO2009/055206 | 4/2009 |
| WO | WO2009/055207 | 4/2009 |

OTHER PUBLICATIONS

PCT/US08/78134: Response to Written Opinion filed Sep. 9, 2009.
PCT/US08/78134: $2^{nd}$ Written Opinion dated Feb. 5, 2010.
PCT/US08/78134: Response to $2^{nd}$ Written Opinion dated Apr. 5, 2010.
PCT/US08/78134: IPRP dated Apr. 22, 2010.
PCT/US08/78099: Search Report and Written Opinion dated Dec. 11, 2008.
PCT/US08/78099: Response to Written Opinion dated Aug. 14, 2009.
PCT/US08/78099: IPRP dated Feb. 2, 2010.
PCT/US08/78125: Search Report and Written Opinion dated Feb. 2, 2009.
PCT/US08/78114: Search Report and Written Opinion dated Feb. 10, 2009.
PCT/US08/78114: Response to Written Opinion dated Aug. 21, 2009.
PCT/US08/78114: IPRP dated Dec. 18, 2009.
PCT/US08/78127: Search Report and Written Opinion dated Dec. 12, 2008.
PCT/US08/78127: Response to Written Opinion dated Jun. 12, 2009.
PCT/US08/78127: IPRP dated Dec. 21, 2009.

* cited by examiner a battery or supercapacitor, within the housing of the IMD. Information regarding the recharging or other use of the power source may be monitored remotely to assure proper functioning of the IMD, e.g., to monitor and maintain proper therapy delivery.

TRANSMISSION OF POWER SOURCE USAGE INFORMATION OVER A NETWORK

This application is a U.S. National Stage filing under 35 U.S.C. 371 of copending PCT Application Serial No. PCT/US2008/78114, filed Sep. 29, 2008; which claims priority to U.S. Provisional Application No. 61/000,159 filed Oct. 24, 2007, entitled "Transmission of Power Source Usage Information Over a Network" the disclosures of each of the above which are incorporated by reference as if re-written herein in their entirety.

TECHNICAL FIELD

The invention relates to medical devices and, more particularly, to implantable medical devices that include a power source.

BACKGROUND

Implantable medical devices (IMDs) are used to deliver therapy, e.g., electrical stimulation therapy or drug delivery therapy, to patients to treat a variety of symptoms or conditions. Example conditions that may be treated by an IMD include chronic pain, tremor, Parkinson's disease, epilepsy, incontinence, gastroparesis, sexual dysfunction, or cardiac arrhythmia. Typically, implantable medical devices deliver therapy to treat the above-identified symptoms or conditions by, for example, directing the therapy to a location proximate to or within the spinal cord, pelvic nerves, stomach, brain, or heart of a patient.

Generally, a clinician uses a programmer, e.g., a computing device capable of communicating with implantable medical devices via device telemetry, to program an implantable medical device for delivery of therapy to a patient. In some cases, such clinician programmers take the form of handheld and/or tablet-type computing devices. Handheld and/or tablet-type clinician programmers can allow for a more natural "bedside" interaction between clinicians and patients during the programming process. Handheld and/or tablet-type clinician programmers can also allow the programmer to be handed off to the patient for entry of symptom and/or therapy efficacy data.

During the course of therapy, a clinician may desire to adjust therapy parameters and/or other system parameters of the IMD. The clinician may use the clinician programmer to adjust therapy or monitor the operation of the IMD. In addition, the patient may use a patient programmer to adjust therapy according to the effectiveness of the therapy being delivered. The patient programmer may be similar to the clinician programmer, but lack some functionality that is not necessary or desired for the patient to use. In this manner, therapy may be flexible to the needs of the patient and information may be retrieved from the IMD in order to provide the most effective overall treatment of the patient's condition.

Some IMDs that deliver a therapy to a patient include a power source, such as a battery, within a housing of the IMD. Furthermore, some IMDs that do not deliver therapy, such as IMDs that include sensors for monitoring a patient, also include a power source within their housings. In some cases, such power sources are rechargeable. For example, some power sources within IMDs are rechargeable by receiving energy from a device external to the patient through transcutaneous energy transfer, an example of which is inductive energy transfer.

SUMMARY

In general, the disclosure is directed to transmitting power source usage information from an implantable medical device (IMD) to a remote networking device via a network. The IMD operates on power supplied by a power source, such as a battery or supercapacitor, within the housing of the IMD. Information regarding the recharging or other use of the power source may be monitored remotely to assure proper functioning of the IMD, e.g., to monitor and maintain proper therapy delivery.

Power source usage information may include power source recharge patterns or effectiveness. Power source usage information may indicate problems with recharging, such as infrequent recharging events, frequent short recharging events, a long period between recharging events, an overdischarged battery, or a low average coupling during recharge. Any power source event or data may be sent to a remote clinician for review. The information may be automatically analyzed by the remote networking device, or by a clinician or other user of the remote networking device. The user or remote networking device may transmit action requests to the IMD, or an external programming device for the IMD, over the network, based upon the power source usage information. Such action requests may include recharging instructions or troubleshooting suggestions to be communicated to the patient, or a request to unlock an overdischarged battery, as examples.

In one embodiment, the invention is directed to a method comprising generating power source usage information related to a power source within an implantable medical device, and transmitting the power source usage information to a remote networking device via a network.

In another embodiment, the invention is directed to a device comprising a processor that generates power usage information related to a power source within an implantable medical device, and a communication circuit that transmits the power source usage information to a remote networking device via a network.

In another embodiment, the invention is directed to a method comprising receiving power source usage information related to a power source within an implantable medical device at a remote networking device via a network, generating an action request based upon the power source usage information, and transmitting the action request from the remote networking device via the network.

In another embodiment, the invention is directed to a remote networking device comprising a communication circuit that receives power source usage information related to a power source within an implantable medical device via a network, and a processor that generates an action request based upon the power source usage information, and controls the communication circuit to transmit the action request from the remote networking device via the network.

In another embodiment, the invention is directed to a system comprising a first device that generates power source usage information related to a power source within an implantable medical device, and transmits the power source usage information via a network, and a second device that receives the power source usage information via the network, generates an action request based upon the power source usage information, and transmits the action request to the first device via the network.

The invention is capable of providing one or more advantages. For example, a medical system according to the invention may allow a clinician to remotely monitor power source usage information without requiring the patient to come to a clinic for an appointment. In addition, the IMD or an external device used with the IMD may transmit the power source usage information upon identifying a power source related event, such as a specified, e.g., improper, recharge pattern.

Further, the remote networking device may allow the clinician to send action requests to the IMD or external device in order to remedy any problems that may arise with the power source of the IMD. These remote monitoring options may reduce clinician time in treating the patient, while maintaining therapy efficacy.

The details of one or more embodiments of the invention are set forth in the accompanying drawings and the description below. Other features, objects, and advantages of the invention will be apparent from the description and drawings, and from the claims.

DETAILED DESCRIPTION

In general, the disclosure is directed to transmitting power source usage information from an implantable medical device (IMD), or an external device that communicates with the IMD, to a remote networking device via a network. Since the IMD generally operates on power supplied by a power source, e.g., battery or capacitor, within the housing of the IMD, it may be beneficial to remotely monitor the operation of the power source. The power source, and the recharging of the power source, may be monitored remotely via the remote networking device. In this manner, power source usage information may be monitored, and power source problems addressed, without requiring a clinic visit. The power source usage information may be transmitted upon a scheduled time, a detected battery event, detecting an available network connection, or a request sent from the remote networking device.

The IMD may generate, store, and transmit the power source usage information. In other embodiments, an external device, e.g., a programmer or recharger, may generate, store, and transmit the power source usage information. In some embodiments, the external device and/or a database may store the power source usage information transmitted by the IMD until it can be or needs to be transmitted to the remote networking device. A clinician may transmit action requests to the IMD or external device over the network based upon the power source usage information.

The power source usage information may include predetermined or specified power source usage patterns, such as infrequent recharging events, frequent short recharging events, a long period between recharging events, an overdischarged power source, a low average coupling between primary and secondary coils for transmission of energy from an external device to the power source, or other improper power source usage patterns. These events may affect the life or performance of the power source, or may indicate unnecessarily high patient burden, and the clinician or remote networking device may be able to take action to reduce or eliminate these undesirable events. For example, the clinician or remote networking device may send an action request to the external programmer that indicates the patient needs to be retrained on appropriate recharging techniques. Alternatively, the clinician or remote networking device may provide an action request to unlock a battery that has shut down due to an improper battery recharge pattern.

Figure 1:
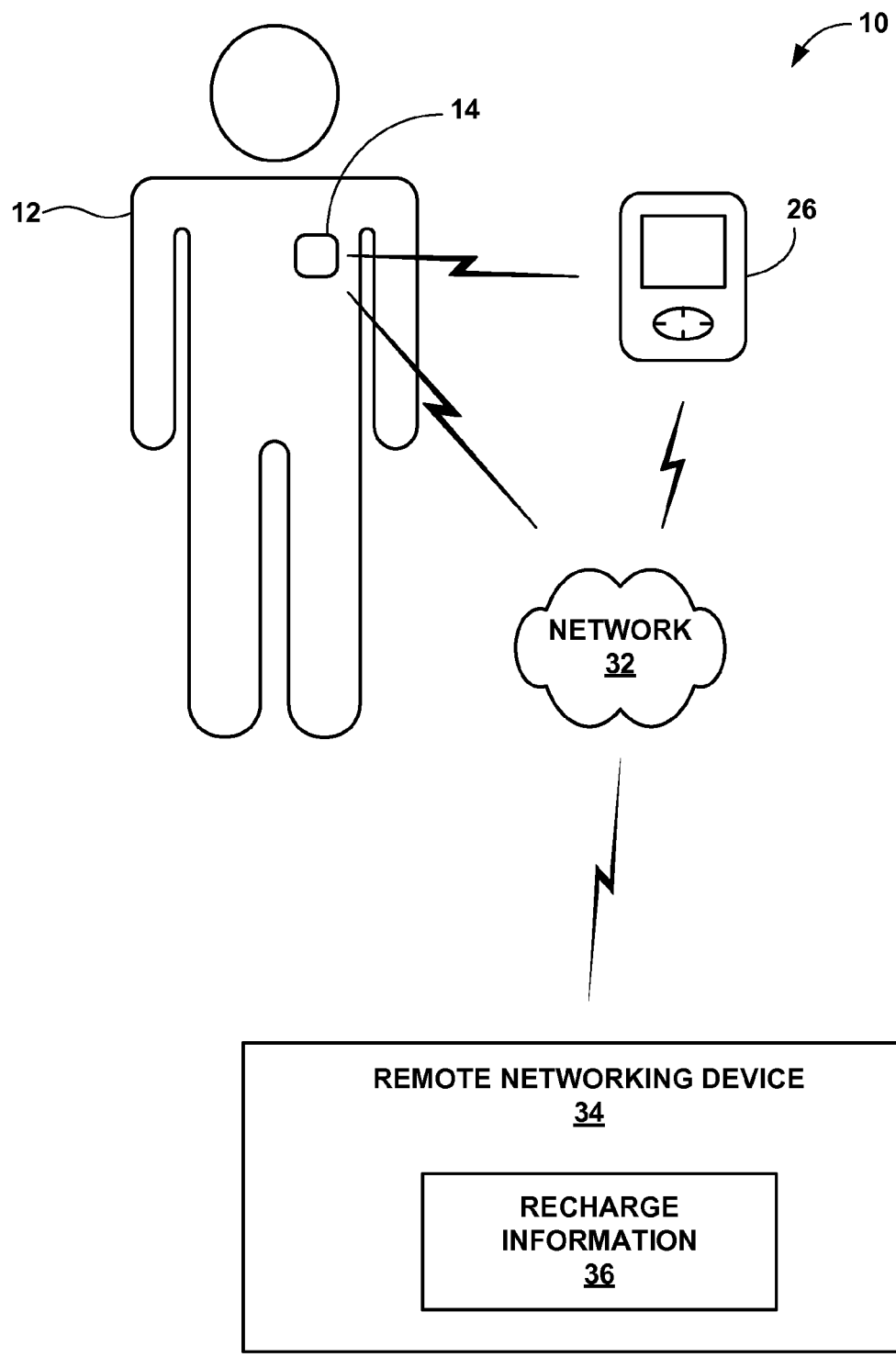
FIG. 1 is a conceptual diagram illustrating an example system that allows power source usage information for an implantable medical device (IMD) to be transmitted to a remote networking device via a network.

FIG. 1 is a diagram illustrating an example system 10 that allows power source usage information for a power source of an implantable medical device (IMD) 14 to be transmitted to a remote networking device 34 via a network 32. System 10 includes an IMD 14, external device 26, and remote networking device 34 that receives power source usage information 36 from either external device 26 or IMD 14 via a network 32. The power source (not shown) of IMD 14 is rechargeable by an external device, such as external device 26. The power source may be, as examples, a rechargeable battery or capacitor.

IMD 14 may deliver electrical stimulation therapy, drug therapy, or both to patient 12. Accordingly, IMD 14 may be an implantable pulse generator that delivers electrical stimulation therapy to patient 12 in the form of electrical pulses, an implantable drug pump that delivers a drug or other agent to patient 12 via a catheter, e.g., for alleviation of pain by intrathecal drug delivery, or a device or devices that deliver both neurostimulation therapy and drug therapy to patient 12. In some embodiments, IMD 14 does not deliver therapy to patient. In some embodiments, IMD 14 includes or is coupled to one or more sensors to monitor patient 12.

IMD 14 may deliver therapy according to one or more programs. Each program may include values for a number of parameters, and the parameter values define the therapy delivered according to that program. In embodiments where IMD 14 delivers electrical stimulation therapy in the form of electrical pulses, the parameters may include voltage or current pulse amplitudes, pulse widths, pulse rates, electrode combinations, polarities of selected electrodes, and the like. In embodiments where IMD 14 includes a drug pump instead of or in addition to an electrical stimulator, program parameters may define flow rates, agent types or concentrations, or infusion types, e.g., continuous or bolus.

External device 26 in FIG. 1 may be an external programmer with which patient 12 interacts to control the delivery of therapy by IMD 14. For example, patient 12 may use external device 26 activate or deactivate therapy and select the program that will be used by IMD 14 to delivery therapy at any given time. Patient 12 may also use external device 26 to make adjustments to programs, such as amplitude or pulse rate adjustments. In other embodiments, external device 26 may be an external charger used by patient 12 to transcutaneously recharge the power source of IMD 14. In some embodiments, external device 26 provides both programmer and recharger functionality.

IMD 14 and external device 26 may communicate with each other via local wireless communication. During a programming session in which a clinician programmer is used to program therapy, the clinician programmer may also communicate with external device 26 and IMD 14 via local wireless communication. For example, external device 26 and a clinician programmer may communicate via wireless communication with IMD 14 using radio-frequency (RF) telemetry techniques known in the art. External device 26 and the clinician programmer may communicate with each other using any of a variety of local wireless communication techniques, such as RF communication according to the 802.11 or Bluetooth specification sets, infrared communication according to the IRDA specification set, or other standard or proprietary telemetry protocols. External device 26 and the clinician programmer need not communicate wirelessly, however. For example, external device 26 and a clinician programmer may communicate via a wired connection, such as via a serial communication cable, or via exchange of removable media, such as magnetic or optical disks, or memory cards or sticks. Further, the clinician programmer may communicate with one or both of IMD 14 and external device 26 via remote telemetry techniques known in the art, communicating via a local area network (LAN), wide area network (WAN), public switched telephone network (PSTN), or cellular telephone network, for example.

As will be described in detail below, external device 26, IMD 14, or both record power source usage information 36 for the power source of IMD 14 during operation of the IMD. Remote networking device 34 may receive power source usage information 36 from external device 26 via network 32. The term "power source usage information" in this disclosure refers to, as examples, power source recharge patterns such as frequency of recharging events, duration of recharging events, period between recharging events, battery discharge state, and degree of coupling between primary and secondary coils during transcutaneous energy transfer. Power source usage information may refer to any other type of power source related performance data desired by the clinician, manufacturer, or technician.

This information may provide insight into the life expectancy or performance of the power source, and may allow action to be taken in time to reduce or eliminate the likelihood of any undesirable events, such as interruption in therapy. Alternately, such information may improve prediction of remaining battery capacity which may serve to improve the accuracy of battery end of life indications provided to the clinician or patient. Remote networking device 34 may present the power source usage information 36 to an authorized user, such as a clinician, technician, or manufacturer, to assist the user in monitoring the power source and/or taking appropriate action. In some examples, power source usage information 36 may be presented as charts, diagrams, histograms, and other graphical representations to allow the user to more easily interpret the information.

Remote networking device 34 may communicate with IMD 14 in real time or on an opportunistic basis. Communication on an opportunistic basis may involve IMD 14 and remote networking device 34 communicating with some intermediate server or other intermediate networking device within network 32 as convenient, e.g., when a network connection is available or a user initiates such communication.

Based upon the power source usage information, the clinician or networking device 34 may determine that IMD 14 should perform some activity. Based on such a determination, remote networking device 34 may transmit an action request to IMD 14 via network 32. Once IMD 14 receives the action request, IMD 14 may perform the action requested in real-time, or at some other scheduled or opportunistic time.

For example, an overdischarged power source may have caused IMD 14 to suspend delivery of therapy. An overdischarged power source may have also caused IMD 14 to disable the ability of the power source to be recharged. In other words, the power source may be set to a locked state by the processor of IMD 14 until usage information 36 able to be reviewed to identify any problems with the power source and/or the patient 12 may be consulted regarding proper recharging techniques. The action request may be directed to a command that unlocks the power source for use. Once the IMD 14 unlocks the power source in response to the action request, patient 12 may recharge the battery and continue therapy.

In some embodiments, power source usage information 36 may be generated and stored within IMD 14 until the information is transmitted to external device 26 and/or remote networking device 34. The processor within IMD 14 may continually or periodically monitor power drawn from the power source, remaining charge in the power source, recharging events, recharging durations, or any other power source related events. In other embodiments, IMD 14 may generate power source usage information 36 and immediately transmit the information to external device 26 or remote networking device 34 via network 32.

System 10 may alter the generation and transmission of power source usage information 36 during therapy. For example, power source usage information 36 may be monitored and transmitted frequently in the time shortly after implantation of IMD 14 to allow review of initial patient 12 recharging technique or any problems with the IMD 14 power source. As patient 12 becomes experienced in using system 10 for therapy, power source information 36 may be monitored less frequently. However, in some embodiments, power source usage information 36 may be monitored or sampled consistently throughout the use of IMD 14.

In one example, IMD 14 communicates with external device 26 and uses the external device as an access point to network 32. In another example, IMD 14 communicates wirelessly to a base station or other device that provides an access point for IMD 14 to network 32. In any case, IMD 14 may transmit power source usage information 36 to remote networking device 34 via network 32. IMD 14, external device 26, remote networking device 34, or any other device of system 10 may implement any number of security protocols to ensure that power source usage information 36 and any other data regarding patient 12 or IMD 14 may not be easily intercepted over network 32. For example, the devices of system 10 may implement private and public key encryption to authenticate data. These and any other security measures known in the art may be implemented to ensure the privacy of patient 12 data.

Network 32 may be any combination of wired or wirelessly connected devices capable of transmitting data between two or more devices. Network 32 may include a local area network (LAN), a wide area network (WAN), a landline telephone network, a cellular phone network, the Internet, a wireless network, or any other communication or data network. Network 32 may be always operating such that power source usage information 36 may be transmitted over network 32 at any time determined by IMD 14, external device 26, remote networking device 34, patient 12, or the clinician. In this manner, power source usage information 36 may be transmitted during a programming session, during and/or immediately after delivery of a program, on demand, according to a schedule, or on an opportunistic basis.

Remote networking device 34 may be any type of device that the clinician may use to review power source usage information 36 and/or generate an action request. For example, remote networking device 34 may be a workstation computer, notebook computer, personal digital assistant (PDA), clinician programmer, or any other computing device with access to network 32 and IMD 14. Remote access to power source usage information 36 may allow the clinician to supervise the efficacy of the patient 12 therapy and the operation of IMD 14, whether the clinician is in the clinic, hospital, home, or any other location away from patient 12. The clinician, or any other user of remote networking device 34, may be required to enter a password in order to access the remote networking device. Alternatively, remote networking device 34 may have a biometric input device that receives a biometric from the clinician before access to the remote networking device is approved.

Power source usage information 36 may be routed through one or more servers before reaching remote networking device 34. For example, power source usage information 36 may be transmitted from IMD 14 to network 32 before reaching a server that further relays the power source usage information. The server may then send the power source usage information 36 to remote networking device 34. The server may be operated by the manufacturer of IMD 14 in order to support the operation of IMD 14 and provide services to patient 12 and the clinician. In some examples, an additional server associated with the hospital or clinic of the clinician may receive power source usage information 36 from the manufacturer server and deliver the power source usage information to remote networking device 34.

The server associated with network 32 may route data to and from IMD 14 or external device 26 through a webpage accessible by remote networking device 34. The webpage may be secure and allow an interface for the clinician to access data from IMD 14, such as power source usage information 36. The webpage may also allow the clinician to send power source usage information 36 for analysis by a technician when the clinician believes that IMD 14 or the power source may be malfunctioning. In essence, the webpage hosted by the server may be the hub of patient 12 therapy. In this manner, remote networking device 34 may be any computing device that simply acts as an access point for the clinician into the therapy of patient 12. Further, the information stored within the server may be made available for analysis by academic or corporate researchers when the data is not private or has been made anonymous. This may serve to increase manufacturer updates or modification to IMD 14 in order to improve therapy. Levels of access to data in the server may be controlled by the server based on user profiles established by an administrator and stored in a memory of the server.

The server may comprise a single computing device or processor, or a plurality of computing devices and/or processors that cooperate to provide the functionality ascribed to the server herein. Data may be stored within a single computing device or memory, or within a plurality of computing devices and/or memories. The server may include a memory that stores program instructions that when executed cause server to perform the functions ascribed to the server herein. The server memory may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

While system 10 is shown in FIG. 1 as including patient 12, IMD 14, external programmer 26, network 32, and remote networking device 34, system 10 may include additional devices as necessary or desired by the manufacturer or clinician. For example, system 10 may include multiple external devices 26 and/or multiple remote networking devices 34. In addition, system 10 may utilize one or more servers, databases, data repositories, or other devices capable of transmitting and storing power source usage information 36. In this manner, system 10 may, in some examples, be capable of connecting many patients 12 with many clinicians located at any location around the world.

Further, in some embodiments, remote networking device 34 may automatically or semi-automatically perform any of the remote power source monitoring methods described herein. In such embodiments, remote networking device 34 may take the form of a server that analyzes power source usage information 36, and automatically interacts with IMD 14 or patient 12 to address any issues revealed by such analysis. Remote networking device 34 may automatically interact with IMD 14 or patient 12 as described herein with limited or no supervision by a clinician. In some embodiments, remote networking device 34 may act semi-autonomously, but may also require approval from a clinician or other remote user prior to providing any instructions to IMD 14, external device 26, or patient 12 via network. In other embodiments, remote networking device 34 may alert the clinician based on an event detected by analysis of the power source usage information.

Figure 2:
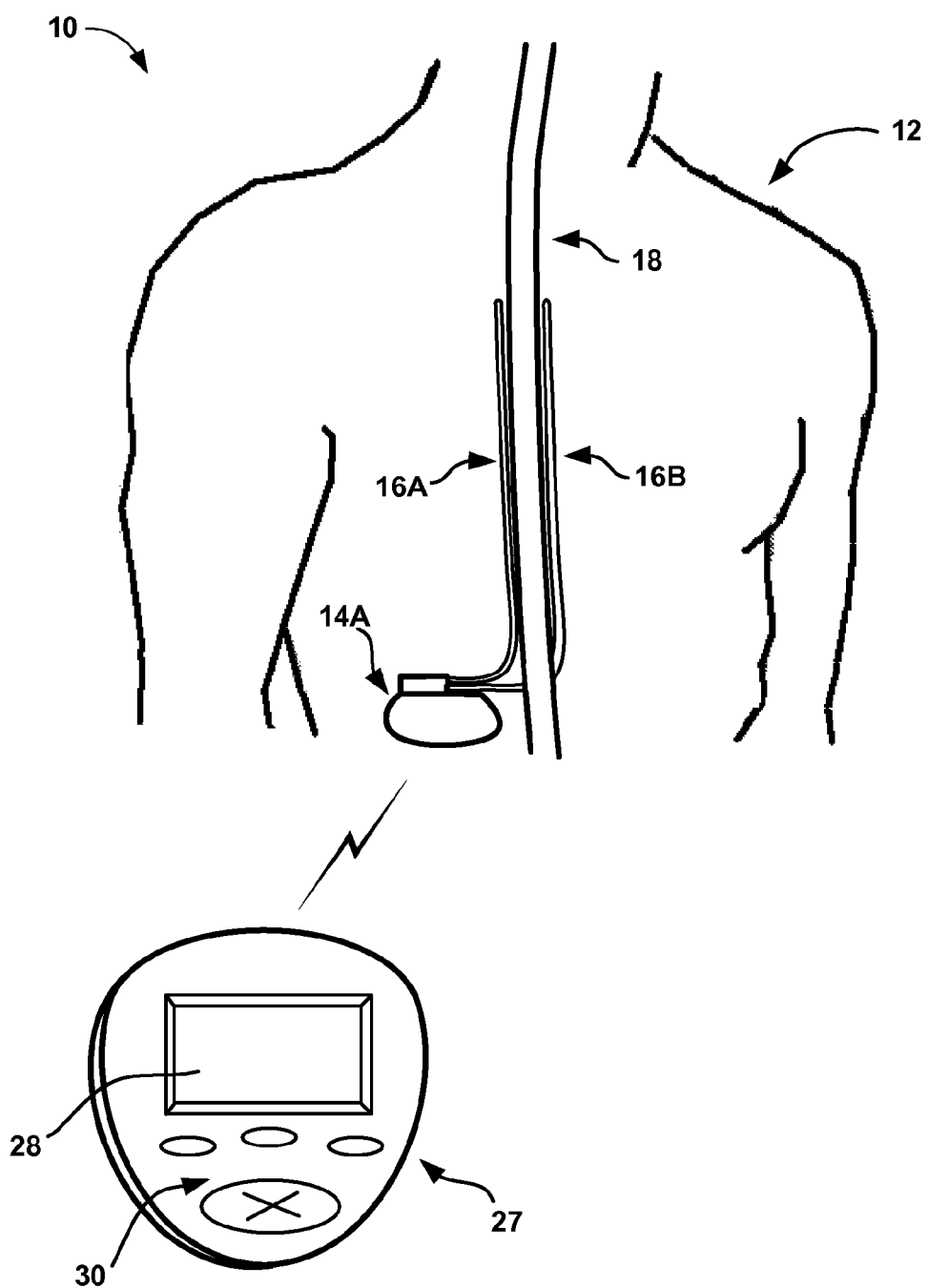
FIG. 2 is a conceptual diagram illustrating an example system for delivering therapy to a patient.

FIG. 2 is a diagram illustrating an example system 10 that includes an IMD 14A that delivers therapy to patient 12. As shown in FIG. 2, IMD 14 delivers electrical stimulation therapy to patient 12 via leads 16A and 16B (collectively "leads 16"). Leads 16 may, as shown in FIG. 2, be implanted proximate to the spinal cord 18 of patient 12, and IMD 14A may deliver spinal cord stimulation (SCS) therapy to patient 12 in order to, for example, reduce pain experienced by patient 12. However, the invention is not limited to the configuration of leads 16 shown in FIG. 2 or the delivery of SCS therapy. For example, one or more leads 16 may extend from IMD 14A to the brain (not shown) of patient 12, and IMD 14A may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14A may deliver neurostimulation therapy to treat incontinence or gastroparesis.

In some embodiments, an IMD 14 delivers therapies other than stimulation to patient 12. For example, in other embodiments, as will be described below, leads 16 may be replaced by catheters which deliver a drug to spinal cord 18, or any of a variety of locations within patient 12 to treat any of a variety of symptoms or disorders. In some examples, IMD 14 may provide a combination electrical stimulation therapy and drug delivery therapy.

As described above, an IMD 14 may deliver therapy according to a program comprising values for a plurality of therapy parameters. In the illustrated embodiment, where IMD 14A delivers electrical stimulation therapy in the form of electrical pulses, the parameters may include voltage or current pulse amplitudes, pulse widths, pulse rates, and the like. Further, each of leads 16 includes electrodes (not shown in FIG. 2), and the parameters for a program may include information identifying which electrodes have been selected for delivery of pulses according to the program, and the polarities of the selected electrodes. In some embodiments, IMD 14A may deliver electrical stimulation therapy according to a group of programs.

Each program of a program group may be designed to address a particular symptom of patient 12. For example, in the case of SCS, each program may be designed to reduce the pain experienced by patient 12 in a different location of the body of patient 12. Further, IMD 14A may deliver electrical stimulation therapy according to multiple programs of a group at substantially the same time. For example, in embodiments where IMD 14A delivers electrical stimulation therapy as electrical pulses, each pulse may be delivered according to a different program of the group. Thus, a series of n pulses may deliver therapy according to n different programs. Delivery of electrical stimulation therapy according to program groups may allow IMD 14A to address the symptoms of patient 12 more completely than if single program therapies were delivered. Moreover, substantially simultaneous delivery of the programs of a program group may make the delivery of electrical stimulation therapy more comfortable for patient 12 to the extent that it prevents patient 12 from sensing program changes.

System 10 also includes a patient programmer 27, which is an embodiment of external device 26 shown in FIG. 1. Patient programmer 27, as shown in FIG. 2, is a handheld computing device. Patient programmer 27 may also include a display 28 and a keypad 30, to allow patient 12 to interact with patient programmer 27. In some embodiments, display 26 may be a touch screen display, and patient 12 may interact with patient programmer 27 via display 28. Patient 12 may also interact with patient programmer 27 using peripheral pointing devices, such as a stylus or mouse.

Patient 12 may use patient programmer 27 to control the delivery of electrical stimulation therapy by IMD 14A. Patient 12 may use patient programmer 27 to activate or deactivate electrical stimulation therapy, and to select the program or program group that will be used by IMD 14A to deliver electrical stimulation therapy from one or more lists of programs or groups. Further, patient 12 may use patient programmer 27 to make adjustments to programs or groups. In addition, patient programmer 27 may receive and store power source usage information 36 in a memory of the patient programmer. Patient programmer 27 may analyze and/or transmit power source usage information 36 to remote networking device 34 via network 32.

Allowing patient 12 greater control over the delivery of electrical stimulation therapy using patient programmer 27 may lead to more effective therapy and efficient use of clinician time. Patient 12 may be able to select programs or groups and make adjustments in order to address changes in symptoms, which may occur throughout the day, or based on changes in the position, posture, or activity of the patient. These modifications and improvements to electrical stimulation therapy may occur without clinician intervention or remote access by a clinician via remote networking device 34. Further, the clinician may be able to spend less time initially programming electrical stimulation therapy for patient 12 by providing a variety of programs or groups at implant from which patient 12 may choose, allowing patient 12 to experiment with, optimize, improve, or tailor the electrical stimulation therapy over time.

System 10 may also include a clinician programmer (not shown) similar to patient programmer 27 and having additional features. The clinician programmer may be a handheld computing device that includes a display, such as a LCD or LED display, to display information to a user. The clinician programmer may also include a keypad which may be used by a user to interact with the clinician programmer. In some embodiments, the display may be a touch screen display, and a user may interact with the clinician programmer via the display. A user may also interact with the clinician programmer using peripheral pointing devices, such as a stylus or mouse. The keypad may take the form of an alphanumeric keypad or a reduced set of keys associated with particular functions. In some embodiments, remote networking device 34 may function similar to the clinician programmer.

A clinician (not shown) may use the clinician programmer to program electrical stimulation therapy for patient 12. As will be described in greater detail below, the clinician may select existing programs or specify programs by selecting program parameter values, and test the selected or specified programs on patient 12. The clinician may receive feedback from patient 12, and store information identifying the programs and rating information associated with the programs as a session log for patient 12. The clinician may use the session log to more quickly select effective programs, which may be included in groups, for delivery of electrical stimulation therapy for patient 12. In addition, the clinician may initially calibrate the sensor to patient 12 activity levels, motions, or postures during the programming session.

Programs or program groups programmed by the clinician using the clinician programmer may be transmitted to and stored within one or both of patient programmer 27 and IMD 14A. Where the programs or groups are stored in patient programmer 27, patient programmer 27 may transmit the program or group selected by patient 12 to IMD 14A for delivery of electrical stimulation therapy to patient 12 according to the selected program or group. Where the programs or groups are stored in IMD 14A, patient programmer 27 may receive a list of programs or groups from IMD 14A to display to patient 12, and transmit an indication of the selected program or group to IMD 14A for delivery of electrical stimulation therapy to patient 12 according to the selected program or group. Either IMD 14A or patient programmer 27 may select a program or program group based on the signal generated by the sensor, and collect sensor information for transmittal to remote networking device 34.

Figure 3:
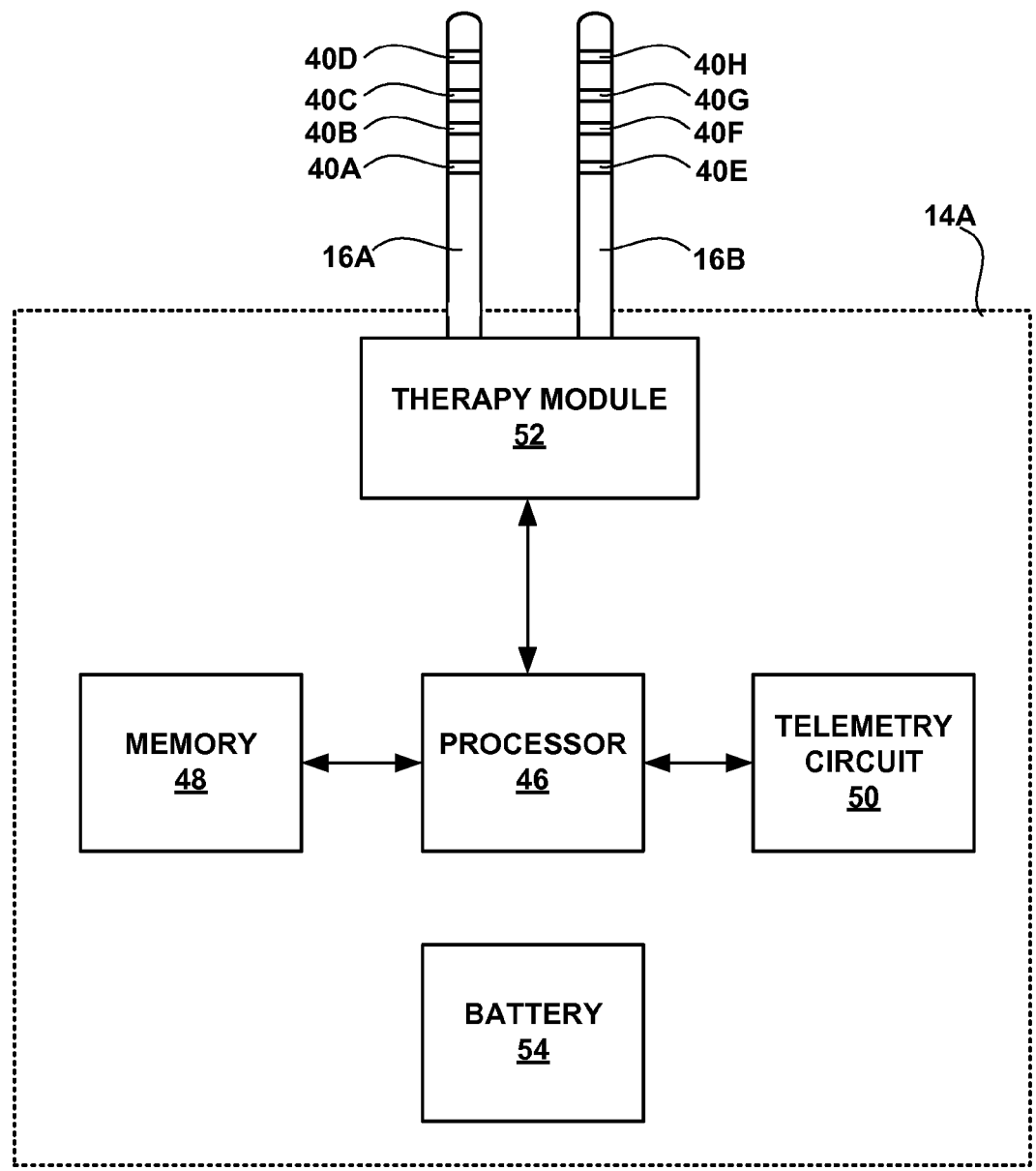
FIGS. 3 and 4 are block diagrams illustrating example implantable medical devices for delivering electrical stimulation therapy and drug delivering therapy, respectively, to the patient according to one or more programs.

FIG. 3 is a block diagram illustrating IMD 14A. IMD 14A may deliver electrical stimulation therapy via electrodes 40A-H of lead 16A and electrodes 40I-P of lead 16B (collectively "electrodes 40"). Electrodes 40 may be ring electrodes, or segmented electrodes, e.g., ring electrodes that are divided into segments that are arranged around the periphery of the lead. The configuration, type and number of electrodes 40 illustrated in FIG. 3 are merely exemplary.

Electrodes 40 are electrically coupled to a therapy module 52 via leads 16. Therapy module 52 may, for example, include an output pulse generator coupled to a power source for IMD 14A, such as a battery 54 in the illustrated embodiment. Alternatively, therapy module 52 may produce continuous electrical signals, e.g. a sine wave. Therapy module 52 may deliver electrical pulses to patient 12 via at least some of electrodes 40 under the control of a processor 46.

Processor 46 controls therapy module 52 to deliver electrical stimulation therapy according to a selected program or program group. Specifically, processor 46 may control therapy module 52 to deliver electrical pulses with the amplitudes and widths, and at the rates specified by the program or group of programs. Processor 46 may also control therapy module 52 to deliver the pulses via a selected subset of electrodes 40 with selected polarities, as specified by the program or group of programs. Processor 46 may control therapy module 52 to deliver each pulse according to a different program of the parameter set. Processor 46 may include a microprocessor, a controller, a DSP, an ASIC, an FPGA, discrete logic circuitry, or the like.

IMD 14A also includes a memory 48. In some embodiments, memory 48 may store programs or program groups that are available to be selected by patient 12 for delivery of electrical stimulation therapy. In some embodiments, processor 46 may generate power source usage information 36, and store usage information 36 in memory 48. Processor 46 may generate power source usage information 36 by monitoring the status and output of battery 54 over the course of therapy. Memory 48 may also include program instructions that, when executed by processor 46, cause IMD 14A to perform the functions ascribed to IMD 14A herein. Memory 48 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

IMD 14A also includes a telemetry circuit 50 that allows processor 46 to communicate with patient programmer 27 (FIG. 2) or another device that connects to network 32. Processor 46 may receive programs to test on patient 12 from the clinician programmer via telemetry circuit 50 during programming by a clinician. Where IMD 14A stores programs or groups in memory 48, processor 46 may receive programs or groups from the clinician programmer via telemetry circuit 52 during programming by a clinician, and later receive program or group selections made by patient 12 from external programmer 26 via telemetry circuit 52. Where external programmer 26 stores the programs or program groups, processor 46 may receive selections made by patient 12 from patient programmer 26 via telemetry circuit 52.

Battery 54 is an example of a power source that delivers operating power to the components of IMD 14A. Battery 54 may be a rechargeable battery that is associated with a power generation circuit to produce the operating power. Recharging may be accomplished through proximal inductive interaction between an external charger and an inductive charging coil within IMD 14A. In some embodiments, power requirements may be small enough to allow IMD 14A to utilize patient motion and implement a kinetic energy-scavenging device to trickle charge battery 54. In other embodiments, non-rechargeable traditional batteries may be used for a limited period of time. In any case, power source usage information 36 may include any data related to the use or charging of battery 54 that may be useful in monitoring therapy, patient 12 actions, or battery life.

Figure 4:
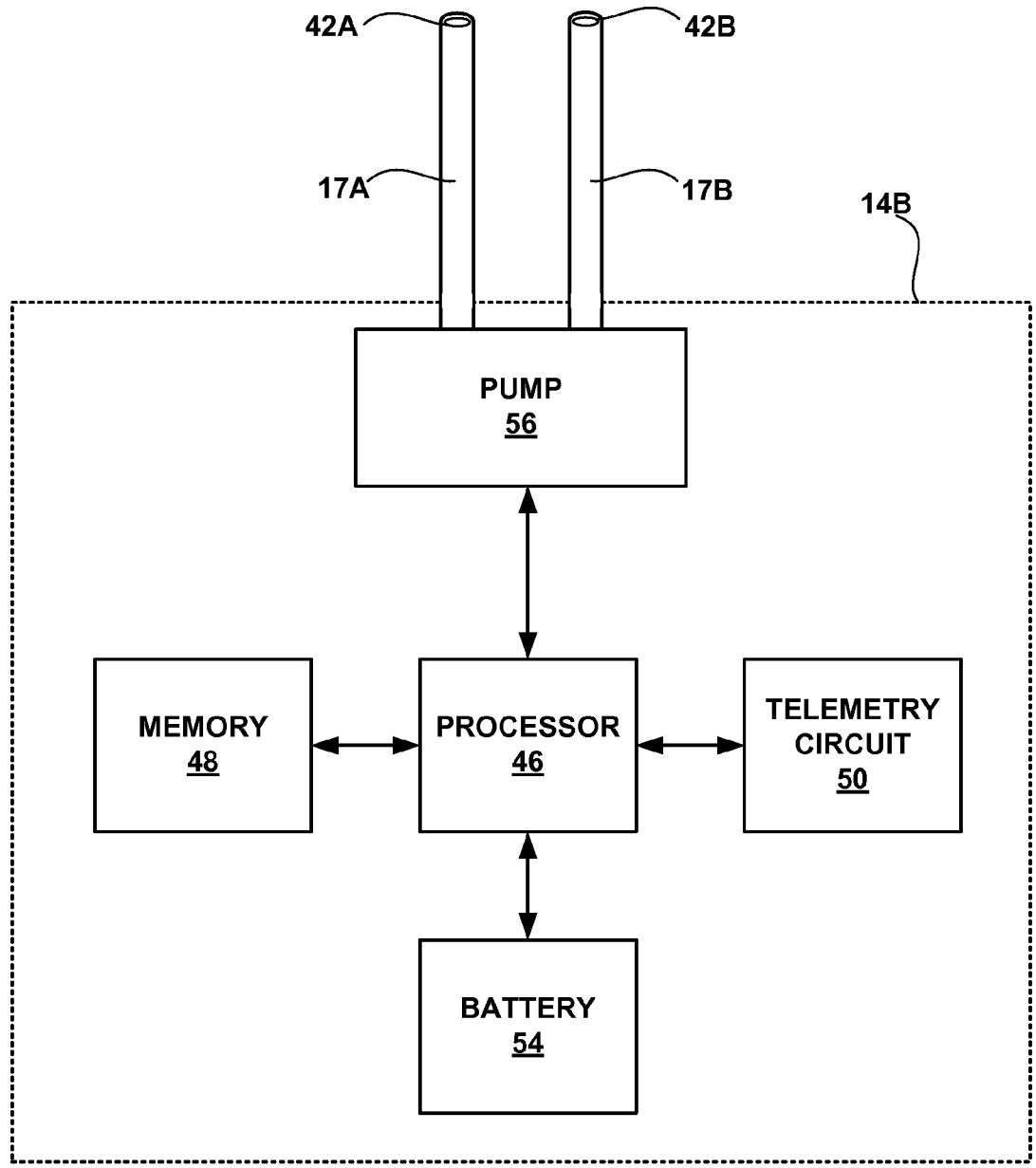

FIG. 4 is a block diagram illustrating an IMD 14B that delivers drug therapy to patient 12 according to one or more programs. IMD 14B is substantially similar to IMD 14A of FIG. 3, but IMD 14B delivers drugs to patient 12 via pump 56. Pump 56 delivers a drug to patient 12 from a reservoir in IMD 14B (not shown), through catheters 17A and 17B (collectively "catheters 17"), and out of ports 42A and 42B (collectively "ports 42"). The configuration, type and number of catheters 17 and ports 42 illustrated in FIG. 4 are merely exemplary. Processor 46 controls pump 56 to deliver the appropriate quantity of drug at the desired frequency defined by one or more programs.

Figure 5:
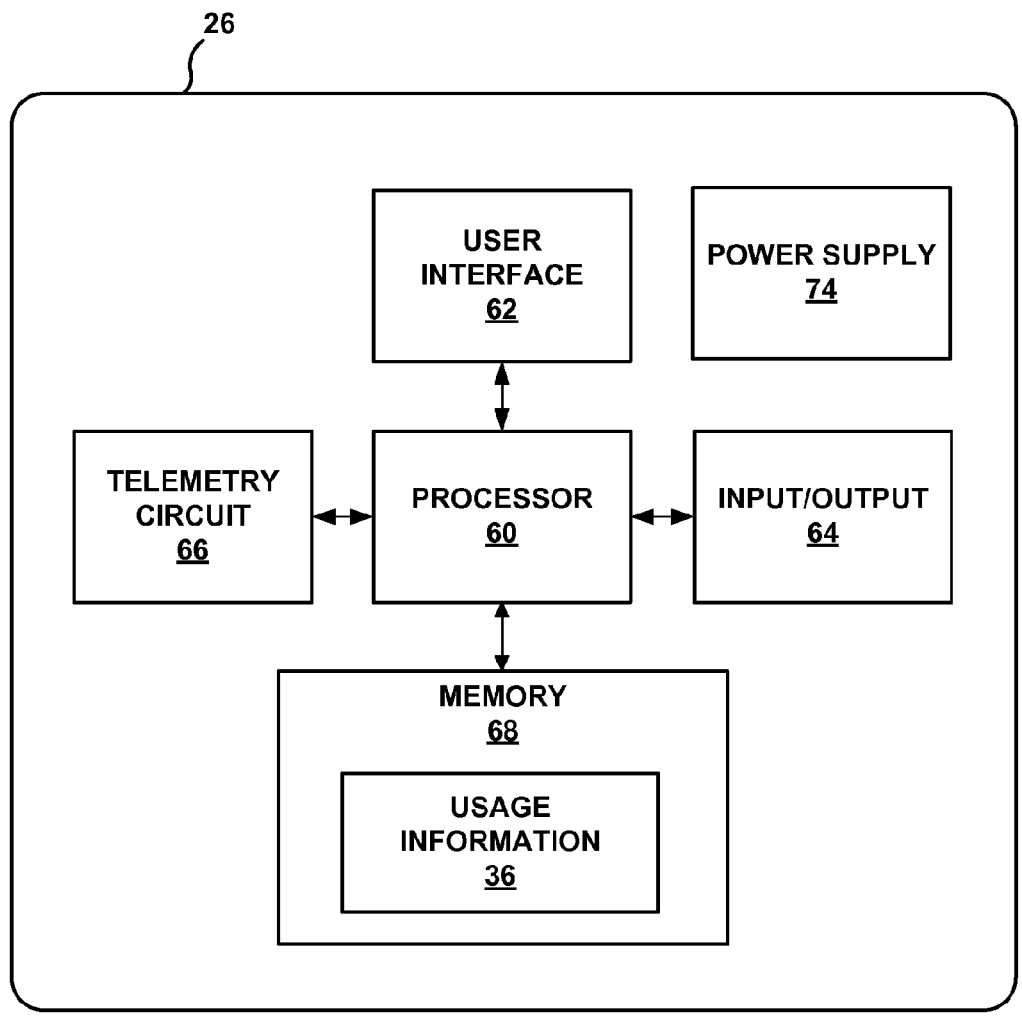
FIG. 5 is a block diagram illustrating an example external programmer that allows control of therapy delivery by the implantable medical device and collects power source usage information.

FIG. 5 is a block diagram illustrating an example external device 26 that collects power source usage information 36. In some embodiments, external device 26 may be a patient programmer 27. However, the invention is not limited to such embodiments.

In other embodiments, external device 26 may take the form of an external charger for IMD 14. In some embodiments, the external charger may be capable of telemetric communication with IMD 14 to receive power source usage information 36 from IMD 14. In some external charger embodiments of external device 26, the charger may collect power source usage information 36, e.g., coupling efficiency, frequency of charging, length of charging, and the like, by monitoring use of the charger. In this manner, the external charger may collect power source usage information without requiring telemetric communication with IMD 14. In some embodiments, external device 26 may provide both external recharger and patient programmer functionality.

In the example illustrated by FIG. 5, external device 26 includes processor 60, user interface 62, input/output (I/O) circuitry 64, telemetry circuitry 66, memory 68, and power supply 74. User interface 62 may include a display, keypad, touch screen, peripheral pointing devices, or any other input devices commonly used with computing devices. Processor 60 may also provide a graphical user interface (GUI) via the display to facilitate interaction with a user. Processor 60 may include a microprocessor, a controller, a DSP, an ASIC, an FPGA, discrete logic circuitry, or the like.

External device 26 also includes a memory 68. Memory 68 may include program instructions that, when executed by processor 60, cause external device 26 to provide the functionality described herein. In addition, memory 68 may include power source usage information 36. Power source usage information 36 may be stored in memory 68 from IMD 14 until external programmer 26 can transmit the information to remote networking device 34. Alternatively, memory 68 may store battery usage information 36 for the duration of therapy. Memory 68 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

In addition to telemetry circuitry 66 for communication with IMD 14, external device 26 includes I/O circuitry 64 for communication via network 32. For example, via telemetry circuitry 66, processor 60 may receive power source usage information 36 from IMD 14. Via I/O 64 and network 32, processor 60 may transmit power source usage information 36 to remote networking device 34.

Power supply 74 may be a battery that is rechargeable or non-rechargeable. The user may recharge the battery of power supply 74 via an AC outlet, inductive coupling, computer Universal Serial Bus (USB), or any other technique known in the art. Alternatively, power supply 74 may draw power from an AC or DC electrical power source when batteries are not necessary. In some cases, battery usage information 36 may include information related to the battery of power supply 74.

Figure 6:
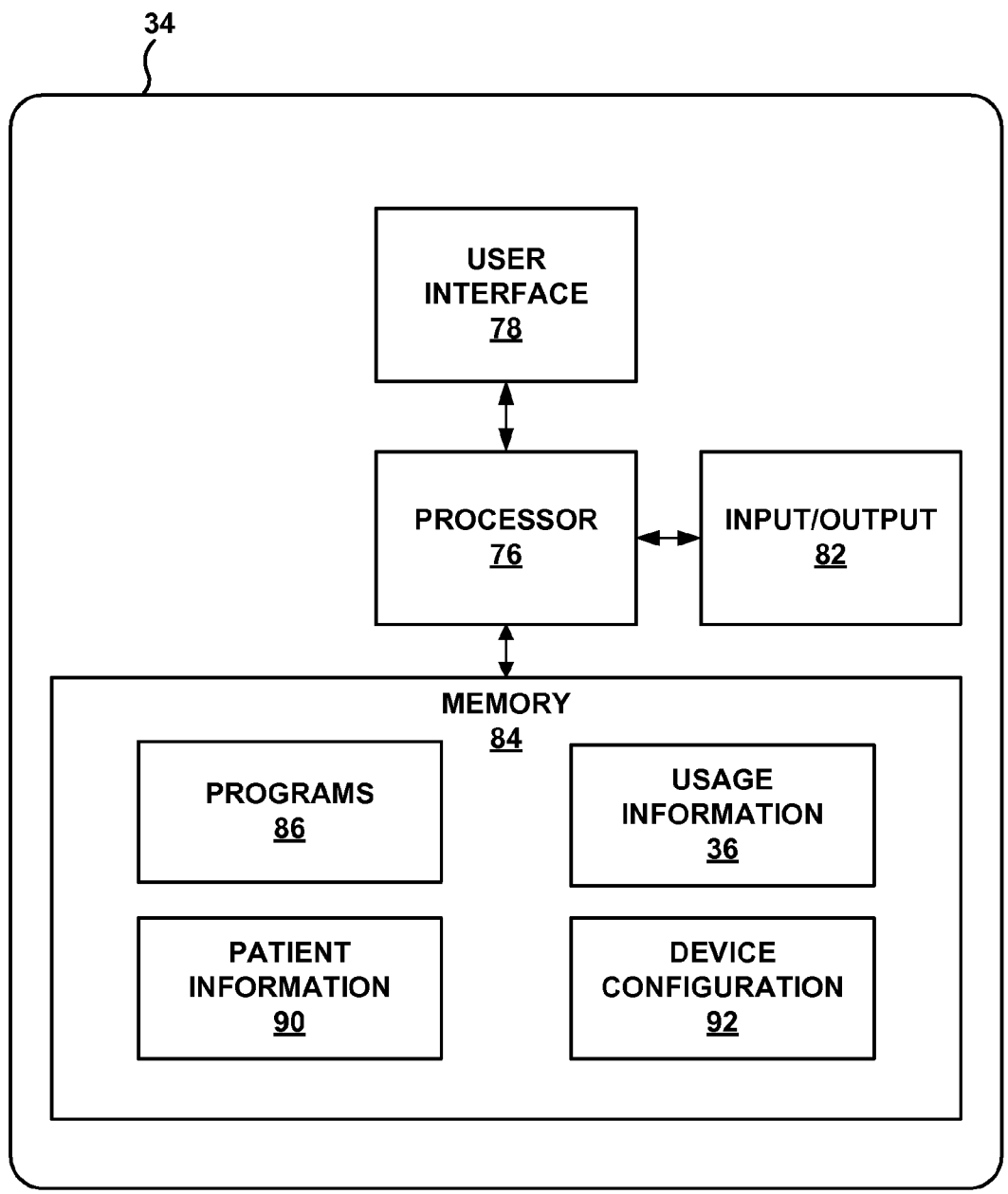
FIG. 6 is a block diagram illustrating an example remote networking device that receives power source usage information via a network and interacts with the IMD or external device in communication with the IMD.

FIG. 6 is a block diagram illustrating an example remote networking device 34 that receives power source usage information 36 from IMD 14 and/or external programmer 26 via a network 32. Remote networking device 34 may be used by a clinician or field technician to communicate with IMD 14 and/or external programmer 26 remotely. Remote networking device 34 may be used to program and adjust stimulation therapy. In addition, remote networking device 34 may be used to receive power source usage information 36 and transmit action requests in response to the power source usage information.

Remote networking device 34 includes processor 76, user interface 78, input/output (I/O) circuitry 82 and memory 84. A user may interact with a processor 76 via a user interface 78 to program stimulation therapy for patient 12, review power source usage information 36, and create and transmit action requests to IMD 14 and/or external device 26, as described herein. User interface 78 may include a display, keypad, touch screen, peripheral pointing devices, or any other input devices commonly used with computing devices such as desktop workstations or notebook computers. Processor 76 may also provide a graphical user interface (GUI) via the display to facilitate interaction with a clinician. Processor 76 may include a microprocessor, a controller, a DSP, an ASIC, an FPGA, discrete logic circuitry, or the like.

Memory 84 may include multiple data sets for each of one or more patients 12. As shown, memory 84 may include programs 86, power source usage information 36, patient information 90 and device configuration information 92. Programs 86 may include individual and groups of programs that each include instructions that IMD 14 may use to deliver therapy to patient 12. Programs 86 may include programs currently used by IMD 14, generated but not transmitted to IMD 14, or used previously by IMD 14. Patient information 90 may include patient condition data, patient history, sensed data, or any other data specifically related to patient 12. Device configuration 92 may include data identifying the configuration of IMD 14 and/or external device 26 in addition to instructions for communication with IMD 14 and/or external device 26. Memory 84 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

I/O circuitry 82 may allow for communications between remote networking device 34 and an access point to network 32 or another device. In this manner, remote networking device 34 may receive power source usage information 36 from IMD 14 and/or external programmer 26. In addition to power source usage information 36, remote networking device 34 may utilize I/O circuitry 82 to transmit any data to other devices when needed. When data is transmitted from remote networking device 34 through I/O circuitry 82, processor 76 may only send data not previously transmitted to the intended device. Alternatively, processor 76 may compare data received from network 32 with the data from remote networking device 34 and only store data not already within the memory of remote networking device 34.

In some examples, remote networking device 34 may include one or more security features that only allow authorized users to access the remote networking device. For example, a user, e.g., the clinician, may be required to enter a username and password into user interface 78 that is unique to the user. Remote networking device 34 may also require other information from the user for authentication. Alternatively, remote networking device 34 may require the user to input a biometric that identifies the user for authentication. The biometric may be entered into a personal identifier device that the user carries and communicates with remote networking device 34 to authorize the user to use the remote networking device. The biometric may also be provided to a biometric scanner built into remote networking device 34. Types of biometrics used by remote networking device 34 may include a fingerprint, heart rate, electrocardiogram, retinal scan, face scan, or any other anatomical or physiological characteristic that may be used to identify the user.

Figure 7A:
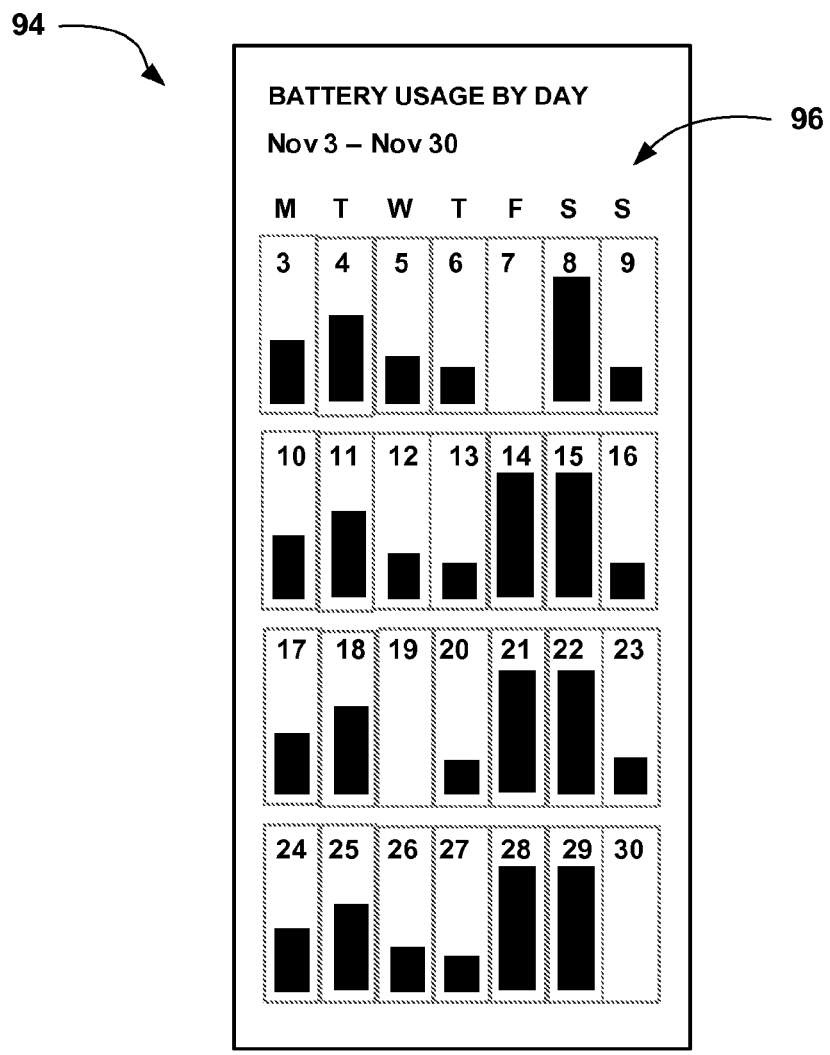
FIG. 7A is an illustration of an example diagram displaying power source usage information by day.

FIG. 7A is an illustration of an example power source usage diagram 94 displaying power source usage information 36 as power consumption 96 by day. As shown in FIG. 7A, power source usage diagram 94 illustrates an example of how some of power source usage information 36 may be provided to a clinician. Power source usage diagram 94 provides detected power consumption 96 for each day during the period of November 3 through November 30, for example. The larger bars for any given day illustrate that more power was consumed by IMD 14 than days with smaller bars. Power consumption 96 may aid the clinician in identifying unusual recharge patterns or power source depletion patterns, in addition to recognizing the amount of therapy received by patient 12.

Bars of diagram 94 are shown without values of the exact power usage and may be used only for illustration. Diagram 94 may be configured to display power consumption 96 over any time period, such as days, weeks, months, or years. The format of diagram 94 may also be modified to show percentages, values, pie charts, or any other visualization format supported by remote network device 34. The clinician may use remote networking device 34 to retrieve more specific power consumption values for each day or other time period to more thoroughly investigate the use of the IMD power source.

Figure 7B:
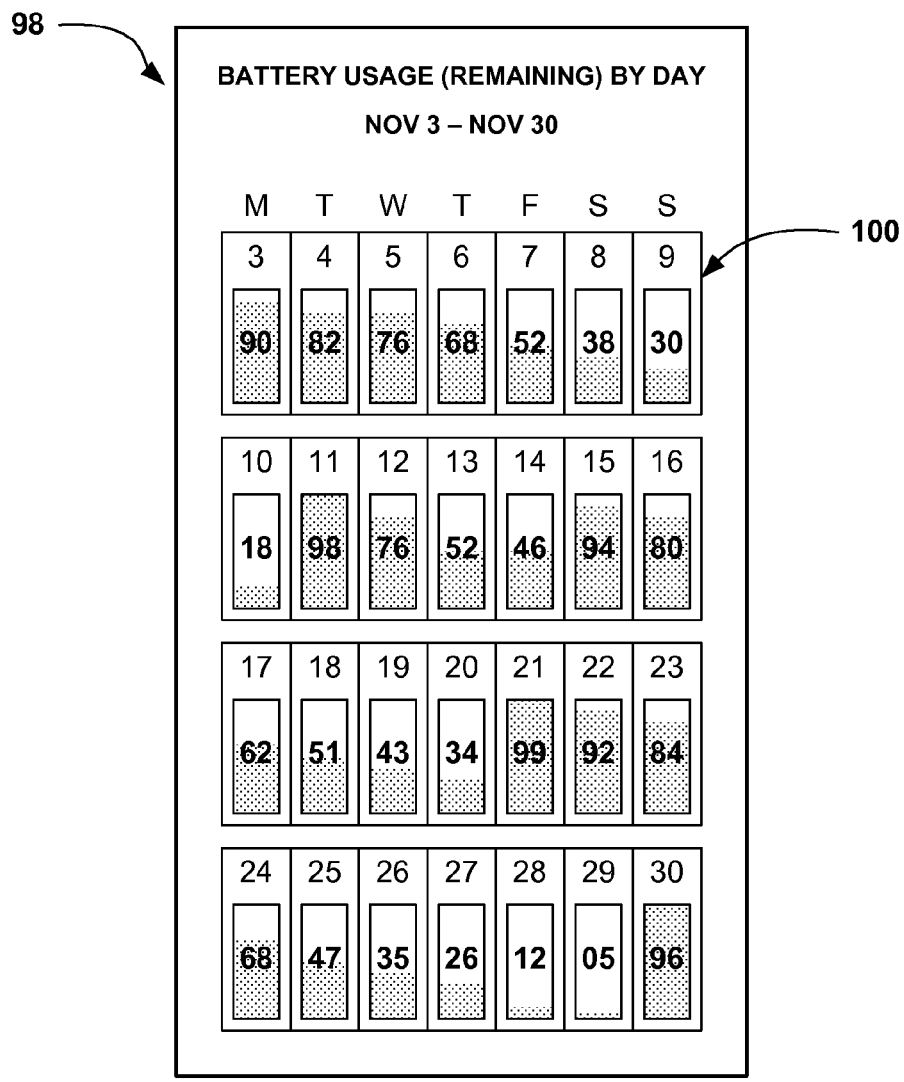
FIG. 7B is an illustration of an example diagram displaying power source usage information, specifically remaining battery power, by day.

FIG. 7B is an illustration of an example power source usage diagram 98 displaying power source usage information 36, specifically remaining battery power 100, by day. As shown in FIG. 7B, power source usage diagram 98 illustrates an example of how some of power source usage information 36 may be provided to a clinician. Power source usage diagram 98 provides detected remaining battery power 100 for each day during the period of November 3 through November 30, for example. For each day in diagram 98, the percentage of remaining battery power 100 is provided in front of a bar that approximates the amount of power remaining. In this manner, the clinician may visualize the status of the IMD 14 battery for each day during the selected period of time. Increases in remaining battery power 100 may indicate that patient 12 recharged the battery. Small increases in battery power may indicate incomplete recharging while very low remaining battery power 100, November 29 for example, indicates that patient 12 is not charging the battery when the battery power is low. Diagram 98 may aid the clinician in identifying unusual recharge patterns or battery depletion patterns, in addition to recognizing the amount of therapy received by patient 12.

Bars of diagram 98 are shown with percentages the exact remaining battery power 100, but diagram 98 is only one example of an indication of the remaining battery power. Diagram 98 may be configured to display remaining battery power 100 over any time period, such as days, weeks, months, or years. The format of diagram 98 may also be modified to show values, pie charts, or any other visualization format supported by remote network device 34. The clinician may use remote networking device 34 to retrieve more specific remaining battery power 100 for each day or other time period to more thoroughly investigate the use of the battery.

Figure 8:
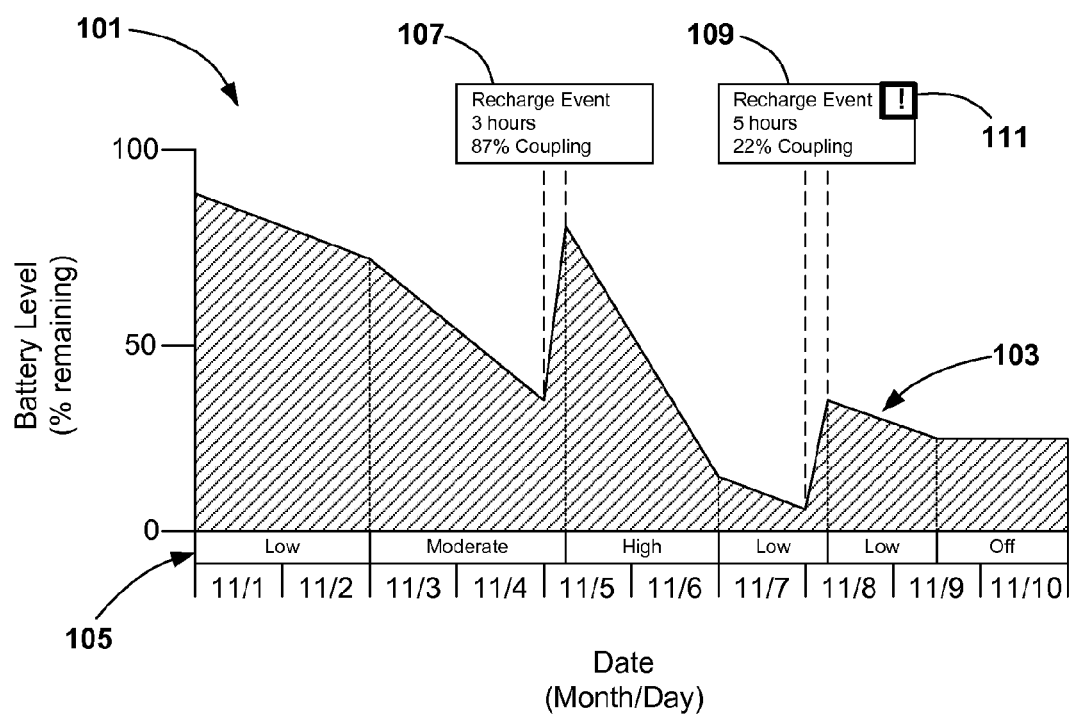
FIG. 8 is an illustration of an example power source usage diagram displaying integrated elements of the power source usage information.

FIG. 8 is an illustration of an example power source usage diagram displaying power source usage information, including charge remaining, recharging events, performance of recharging events and therapy settings, in an integrated manner. As shown in FIG. 8, diagram 101 displays information relevant to the power that is used during stimulation therapy of patient 12 matched to the date of the usage. Diagram 101 includes power source status 103, recharge event windows 107 and 109, and therapy setting indication 105. Patient 12 or the clinician may change the settings of display 101 to include the power source usage information desired by the user. Diagram 101 illustrates that the power source usage information may be correlated or matched to therapy settings, e.g., therapy parameters, to identify how therapy affects the power usage.

Power source status 103 is a graph of the battery level, or power remaining in battery 54. Power source status 103 is provided as percent power remaining, but the status may be provided measured battery voltage, remaining time for therapy, or another measure of battery power. As shown, the battery level declines with therapy delivery. The battery level of power source status 103 declines as a function of therapy status 105. When therapy status is low, e.g., 11/1 and 11/2, power source status 103 declines slowly. This is because the low therapy status signifies a low intensity of stimulation therapy. However, increasing the intensity of stimulation therapy more quickly decreased the battery level. For example, power source status 103 declines rapidly when the therapy setting 105 is set to High on 11/5 and 11/6.

Diagram 101 may also provide recharge event windows 107 and 109 to indicate when patient 12 attempted to recharge battery 54 of IMD 14. Recharge event window 107 indicates that the recharge event lasted for three hours with a coupling efficiency of 87 percent, e.g., 87 percent of the energy provided by an external charging device was received by IMD 14. Higher coupling efficiencies indicate that the inductive coupling between the charger and battery 54 allows for more efficient transfer of power to battery 54. Lower coupling efficiencies may indicate that patient 12 is not placing the charger close enough to IMD 14. As shown in recharge event window 109, the recharge event had a duration of 5 hours with a low coupling efficiency of 22 percent. The low coupling efficiency beginning 11/7 caused alert 111 to appear within recharge event window 109. Alert 111 is provided to highlight the poor coupling. If the clinician recognizes alert 111 a number of times, the clinician may review correct recharging techniques with patient 12 in order to increase the coupling rates and recharging efficiency.

Diagram 101 may also be interactive. The user, patient 12 or the clinician, may select any portion of power source status 103 to review specific therapy information corresponding to that point in time. In addition, the user may be able to select a particular portion of therapy setting 105 in order to review the specific therapy parameters defining the stimulation therapy, e.g., pulse amplitude, rate or width, or electrode configuration. Diagram 101 may be displayed on external device 26 or remote networking device 34. Diagram 101 may be useful to, for example, the clinician as an indication to the therapy efficacy and/or patient 12 therapy behavior.

Figure 9:
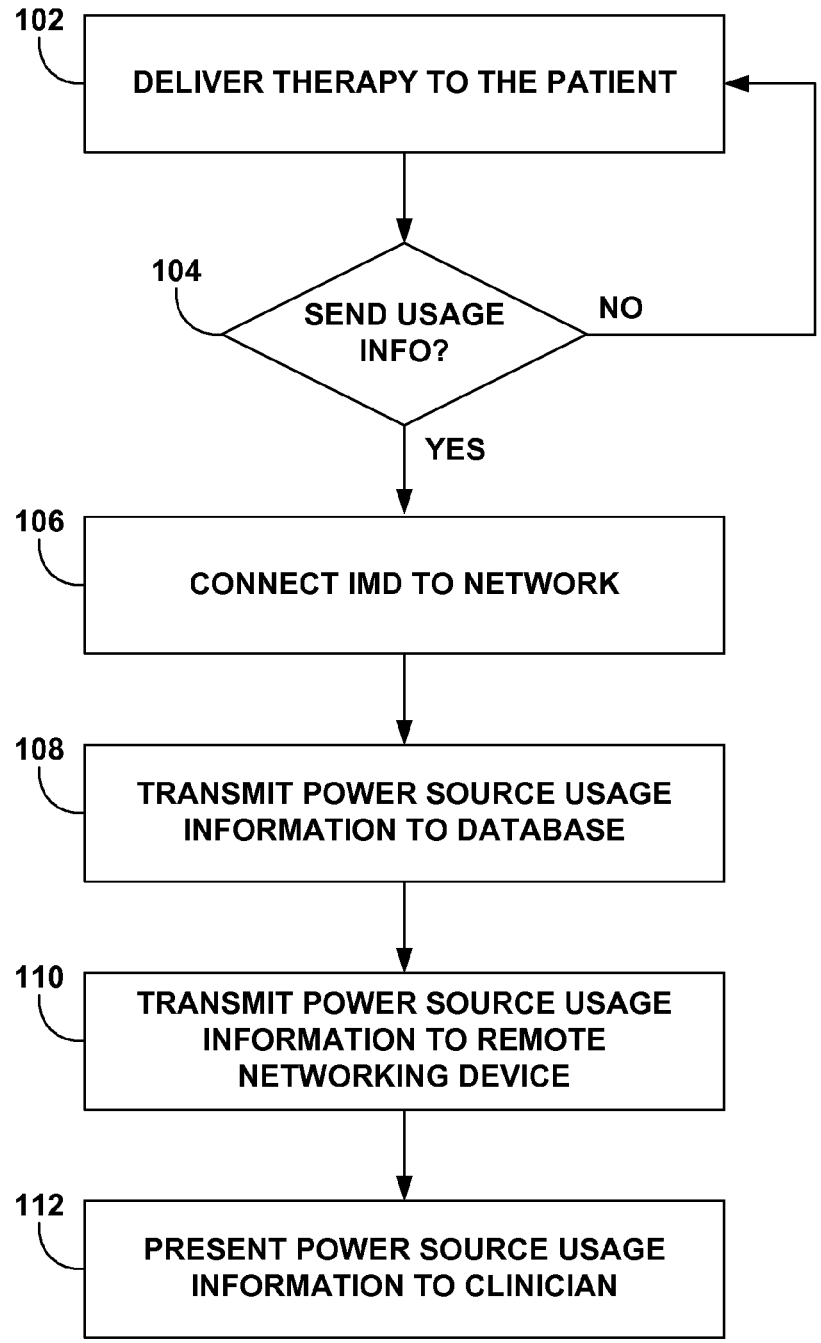
FIG. 9 is a flow diagram illustrating an example technique for transmitting power source usage information at a determined time.

FIG. 9 is a flow diagram illustrating an example technique for transmitting power source usage information 36 at a determined time. As shown in FIG. 9, IMD 14 delivers therapy to patient 12 according to one or more programs stored in memory 48 of the IMD (102). IMD 14 monitors transmission instructions stored within memory 48 to determine when IMD 14 should transmit power source usage information 36 (104). The transmission instructions may include a transmission schedule that instructs IMD 14 to transmit power source usage information 36 a one or more times during a day, week, or month. Alternatively, the transmission schedule may instruct IMD 14 to transmit power source usage information 36 at predetermined intervals during therapy or after a power source event, such as a recharge event. Transmission instructions stored within IMD 14 may alternatively instruct IMD 14 to transmit power source usage information 36 once specified power source recharge patterns, such as infrequent recharging events, frequent short recharging events, a long period between recharging events, an overdischarged battery, and a low average coupling status, are identified by the IMD. Transmission instructions may instruct IMD 14 to send power source usage information 36 based upon and predetermined time or event. If IMD 14 is not instructed to transmit power source usage information 36, IMD 14 continues to deliver therapy to patient 12.

Once IMD 14 is instructed to transmit or send power source usage information 36, IMD 14 connects to network 32 via external programmer 26 or another access point (106). IMD 14 then transmits power source usage information 36 to a data base of the server of network 32 (108). When the server is able, the server transmits power source usage information 36 to remote networking device 34 (110). Remote networking device 34 then presents power source usage information 36 to the clinician via user interface 78 (112). The clinician may interact with remote networking device 34 in order to view power source usage information 36 in a format or analyzed in any desired configuration. In this manner, the clinician may remotely review power source usage information 36 from IMD 14 implanted within patient 12.

Figure 10:
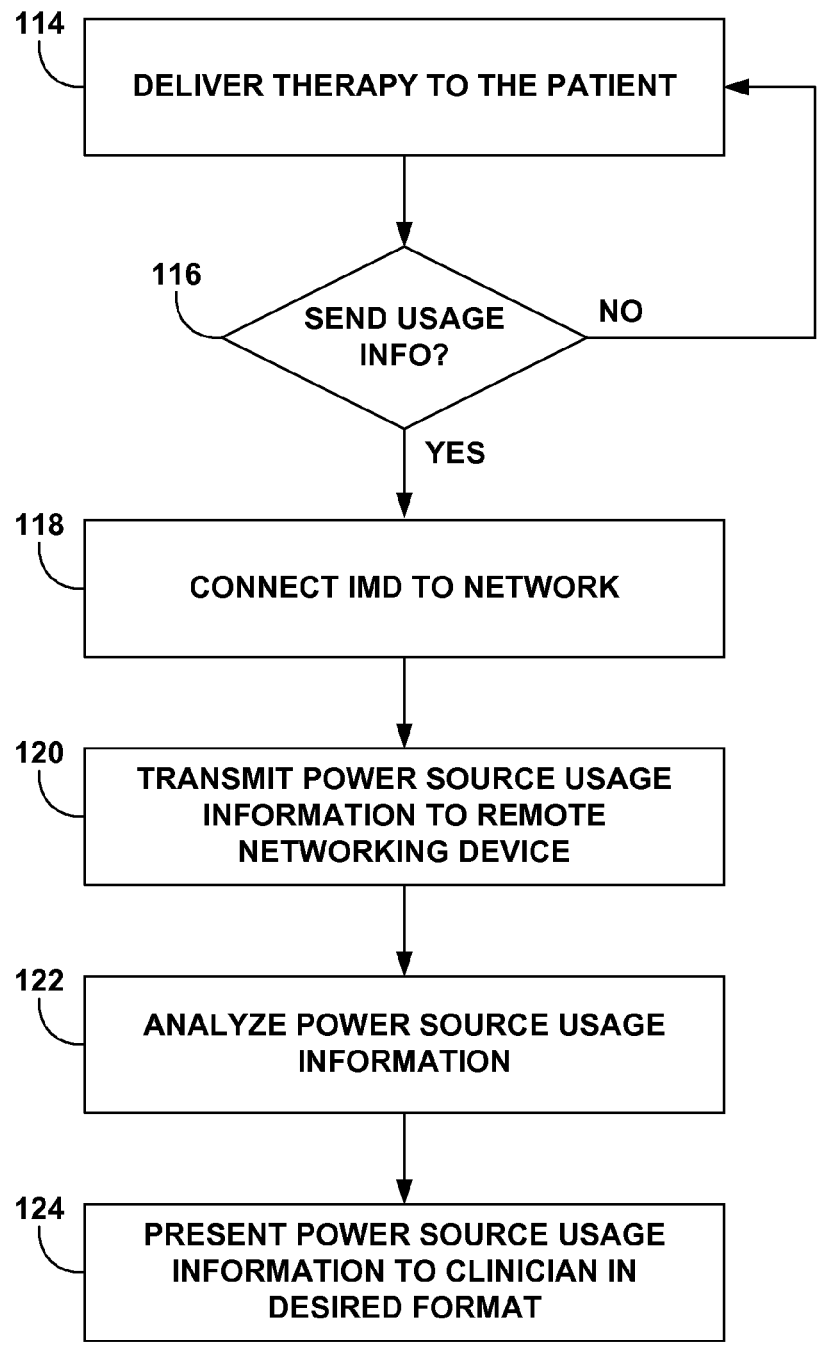
FIG. 10 is a flow diagram illustrating an example technique for transmitting power source usage information at a determined time and analyzing the information at the remote networking device.

FIG. 10 is a flow diagram illustrating an example technique for transmitting power source usage information 36 at a determined time and analyzing the information at the remote networking device 34. As shown in FIG. 10, IMD 14 delivers therapy to patient 12 according to one or more programs stored in memory 48 of the IMD (114). IMD 14 monitors transmission instructions stored within memory 48 to determine when IMD 14 should transmit power source usage information 36 (116). If IMD 14 is not instructed to transmit power source usage information 36, IMD 14 continues to deliver therapy to patient 12 (114).

Once IMD 14 is instructed to transmit or send power source usage information 36, IMD 14 connects to network 32 via external programmer 26 or another access point (118). IMD 14 then transmits power source usage information 36 to the server of network 32 en route to remote networking device 34 (120). Remote networking device 34 then analyzes raw power source usage information 36 according to instructions selected by the clinician or manufacturer (122). Remote networking device 34 then presents analyzed, e.g., summarized, power source usage information 36 to the clinician via user interface 78 (124). The clinician may interact with remote networking device 34 in order to view power source usage information 36 as analyzed by remote networking device 34. In this manner, power source usage information 36 is not analyzed by IMD 14 or external programmer 26 in order to reserve resources available to patient 12 and necessary for therapy delivery.

Figure 11:
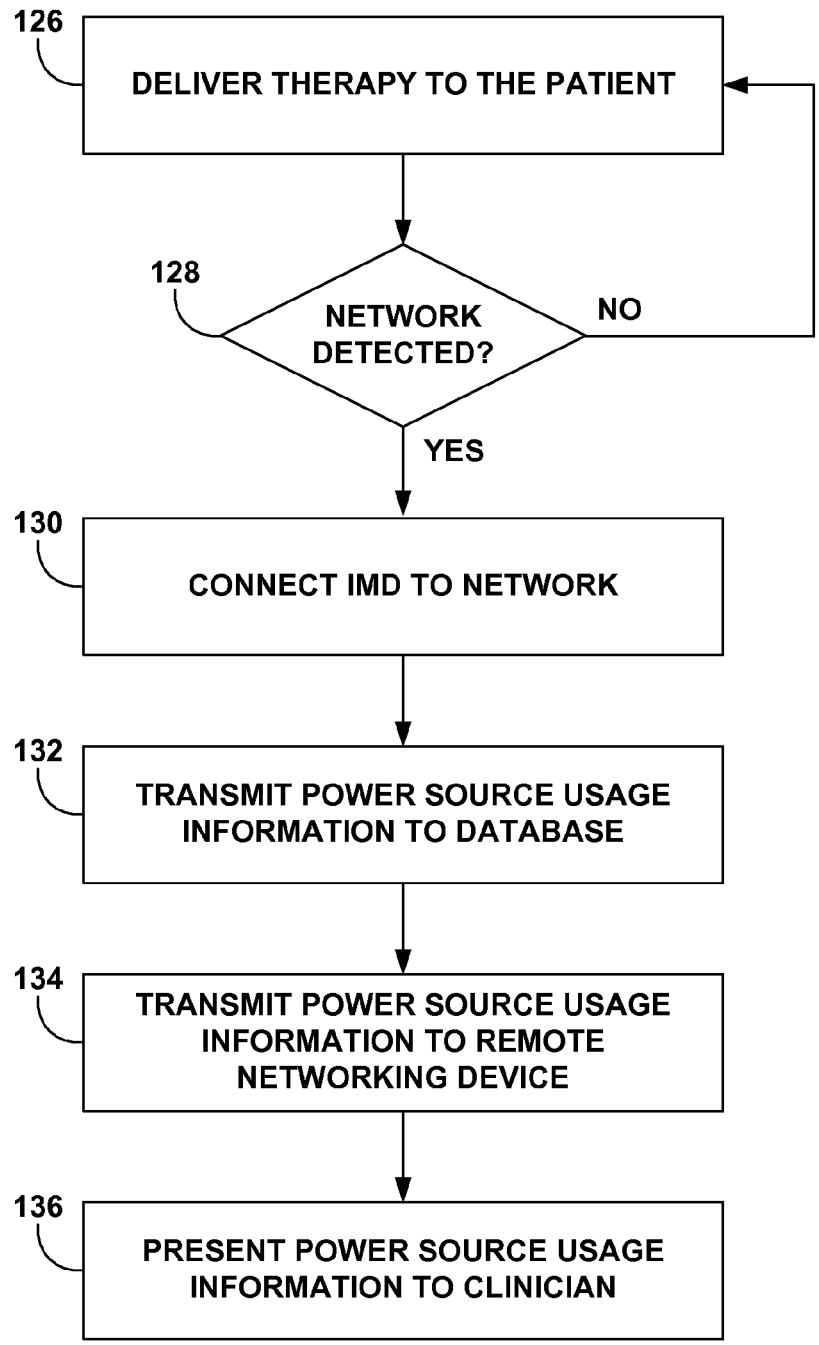
FIG. 11 is a flow diagram illustrating an example technique for transmitting power source usage information when a network is detected.

FIG. 11 is a flow diagram illustrating an example technique for transmitting power source usage information 36 when network 32 is detected. As shown in FIG. 11, IMD 14 delivers therapy to patient 12 according to one or more programs stored in memory 48 of the IMD (126). Telemetry circuit 50 continually monitors the availability of network 32. In other embodiments, external programmer 26 may monitor the availability of network 32 and subsequently notify IMD 14 via telemetry circuit 50 when the network is available. If network 32 is not detected (128), IMD 14 just continues to deliver therapy to patient 12. If network 32 is detected (128), telemetry circuit 50 connects IMD 14 to network 32 (130). In this manner, IMD 14 transmits power source usage information 36 on an opportunistic basis. Once connected to network 32, IMD 14 may continue to deliver therapy to patient 12. In alternative embodiments, telemetry circuit 50 may only monitor availability of network 32 when IMD 14 has power source usage information 36 to transmit.

IMD 14 then transmits power source usage information 36 to a data base of the server of network 32 (132). When the remote networking device 34 is available, the server transmits power source usage information 36 to remote networking device 34 (134). Remote networking device 34 then presents power source usage information 36 to the clinician via user interface 78 (136). The clinician may interact with remote networking device 34 in order to view power source usage information 36 in a format or analyzed in any desired configuration. In this manner, the clinician may remotely review power source usage information 36 from IMD 14 implanted within patient 12.

Figure 12:
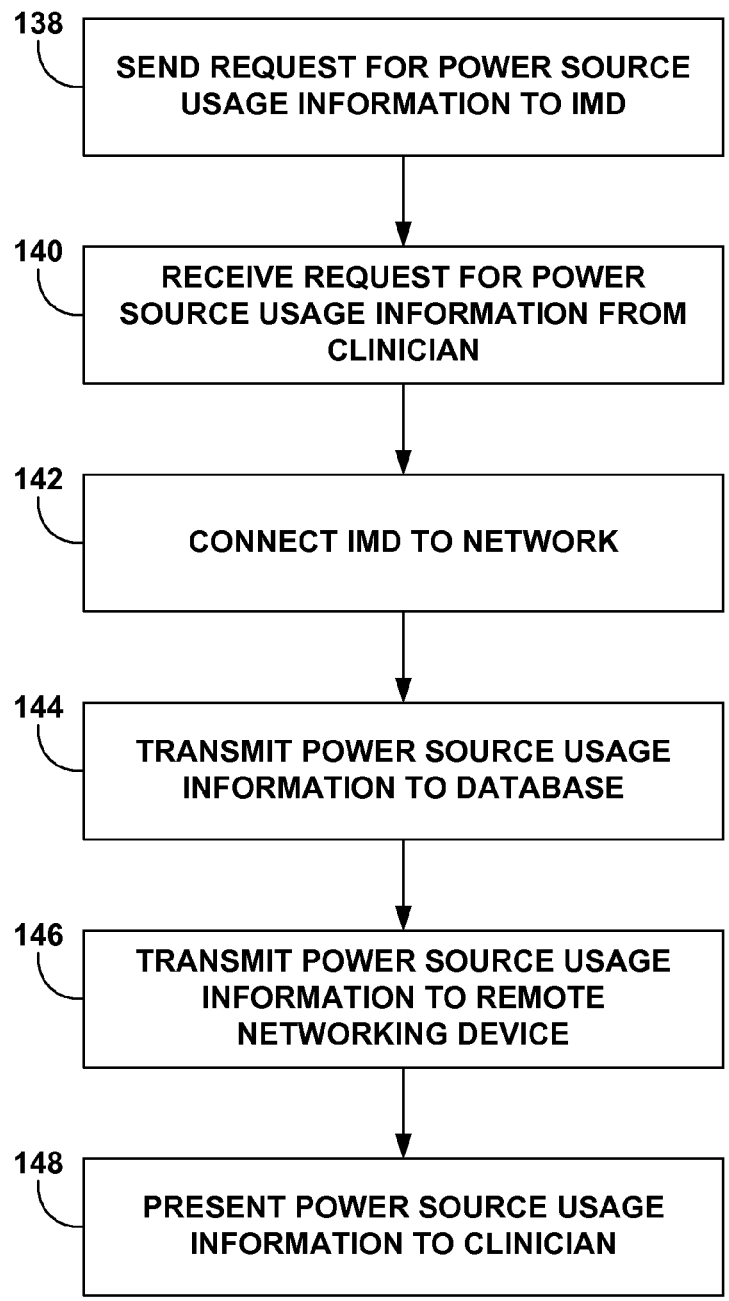
FIG. 12 is a flow diagram illustrating an example technique for transmitting power source usage information after a request has been received.

FIG. 12 is a flow diagram illustrating an example technique for transmitting power source usage information 36 after a battery usage request has been received by IMD 14. As shown in FIG. 12, a clinician sends a power source usage request to IMD 14 during the deliver of therapy by IMD 14 (138). The clinician may send the power source usage request from remote networking device 34 via network 32 in order to receive battery usage information 36 from IMD 14. When IMD 14 is connected to network 32, IMD 14 receives the power source usage request for battery usage information 36 from remote networking device 34 (140). IMD 14 may then generate or retrieve power source usage information 36 and connect to network 32 if the connection to network 32 has been interrupted (142).

IMD 14 then transmits power source sage information 36 to a data base of the server of network 32 (144). When the remote networking device 34 is available, the server transmits power source usage information 36 to remote networking device 34 (146). Remote networking device 34 then presents power source usage information 36 to the clinician via user interface 78 (148). The clinician may interact with remote networking device 34 in order to view power source usage information 36 in a format or analyzed in any desired configuration. In this manner, the clinician may remotely review power source usage information 36 from IMD 14 implanted within patient 12 at any time during therapy.

Figure 13:
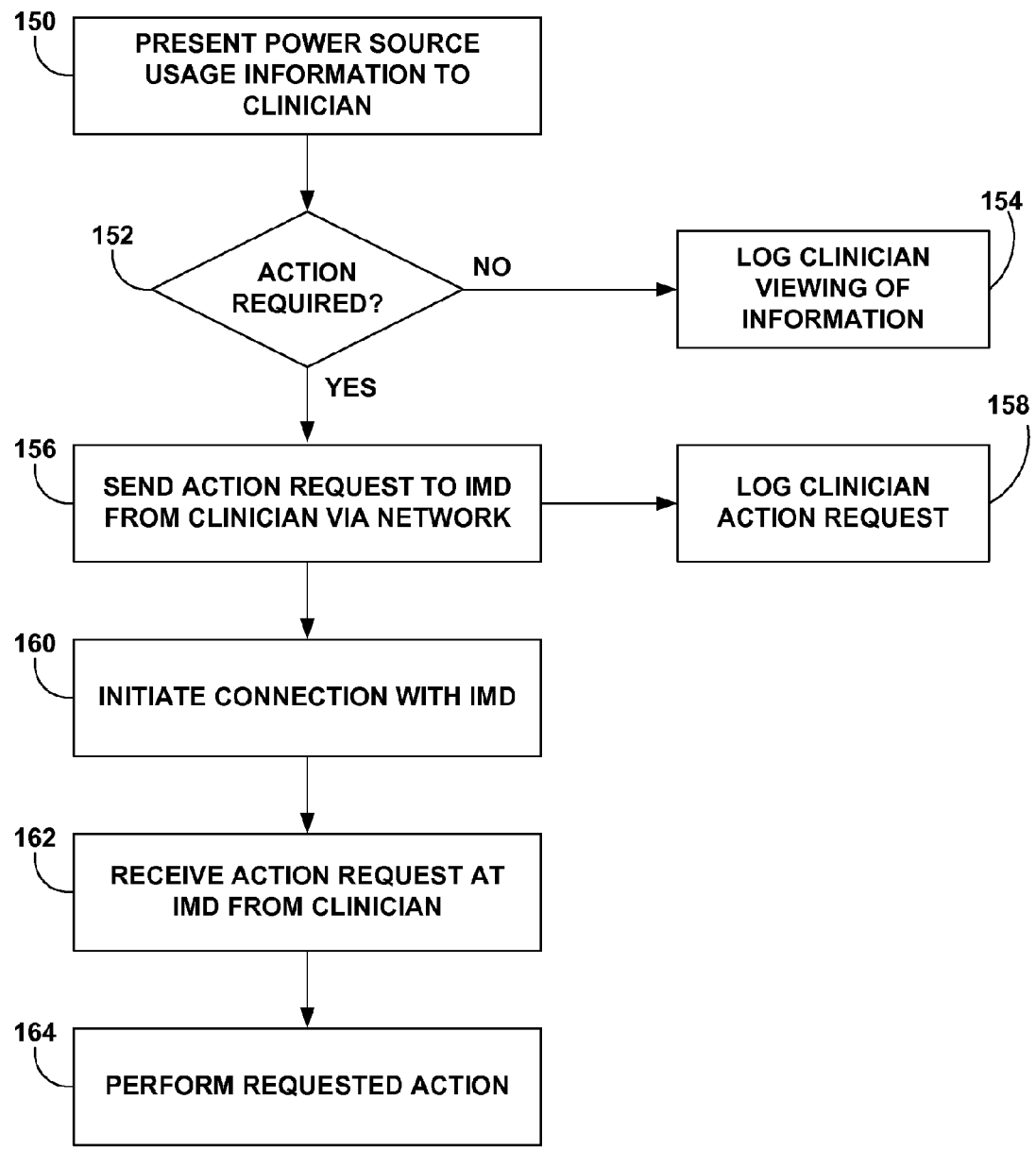
FIG. 13 is a flow diagram illustrating an example technique for transmitting an action request via the network based upon the power source usage information received via the network.

FIG. 13 is a flow diagram illustrating an example technique for transmitting an action request to IMD 14 via network 32 based upon the battery usage information 36 sent by the IMD. As shown in FIG. 13, power source usage information 36 transmitted to remote networking device 34 is presented to the clinician (150). Remote networking device 34 may determine if an action is required on the part of the clinician due to the nature of power source usage information 36 (152). An action may be required from the clinician to unlock a battery that has been fully depleted and entered into a locked state, for example. Such an event would prevent IMD 14 from delivering therapy to patient 12, so the clinician may need to intervene in order for therapy to continue. If an action is not required (152), remote networking device 34 may log that the clinician viewed power source usage information 36 (154).

If an action is required (152), the clinician may use remote networking device 34 to send an action request to IMD 14 via network 32 (156). Remote networking device 34 logs the clinician action request for confirmation that the clinician attempted to act on the reviewed power source usage information 36 (158). Once the action request is sent by remote networking device 34 to the server of network 32, the server initiates a connection with IMD 14 (160). The connection between IMD 14 and the server may be in real time or delayed until the subsequent time that IMD 14 connects to network 32. IMD 14 then receives the action request from the server (162). Alternatively, IMD 14 may receive the action request through external programmer 26 communicating with network 32. Once IMD 14 receives the action request, IMD 14 performs the requested action (164). In the case of a locked battery, IMD 14 may unlock the battery so that patient 12 may resume stimulation therapy. In some embodiments, IMD 14 may transmit a confirmation message to remote networking device 34 indicating the action that was performed and the resulting status of IMD 14. The clinician may send another action request if the IMD 14 status is not satisfactory to the clinician.

Various embodiments of the invention have been described. However, one skilled in the art will recognize that various modifications may be made to the described embodiments without departing from the scope of the invention. For example, the invention may be embodied as a computer-readable medium that includes instructions to cause a processor to perform any of the methods described herein. These and other embodiments are within the scope of the following claims.

The invention claimed is:

1. A method comprising:
generating, by at least one of an external device or an implantable medical device, power source usage information related to recharging of a rechargeable power source within the implantable medical device, wherein the power source usage information describes a plurality of previous recharging events of the rechargeable power source;
analyzing, by at least one of the external device, the implantable medical device, or a remote networking device, the plurality of previous recharging events to identify a plurality of recharge patterns of the plurality of previous recharging events;
detecting, by at least one of the external device, the implantable medical device, or the remote networking device, at least one improper recharge pattern of the plurality of recharge patterns based on at least some previous recharging events of the plurality of previous recharging events,
wherein the at least one improper recharge pattern comprises at least one of infrequent recharging events, frequent short recharging events, a long period between recharging events, or a low degree of coupling between primary and secondary coils during transcutaneous energy transfer to the rechargeable power source; and
receiving, by at least one of the external device or the implantable medical device, an action request from the remote networking device via a network in response to the detection of the at least one improper recharge pattern.

2. The method of claim 1, wherein the power source usage information further indicates at least one of frequency of recharging events, duration of recharging events, period between recharging events, or degree of coupling between primary and secondary coils during transcutaneous energy transfer to the power source.

3. The method of claim 1, wherein the action request comprises a patient instruction regarding a power source recharging technique.

4. The method of claim 1, wherein the implantable medical device analyzes the plurality of previous recharging events to identify the plurality of recharge patterns, and wherein the implantable medical device detects the at least one improper recharge pattern, the method further comprising, prior to receiving the action request:

in response to detection of the at least one improper recharge pattern, transmitting, by at least one of the external device or the implantable medical device, the power source usage information to the remote networking device via the network.

5. The method of claim 1, wherein the external device analyzes the plurality of previous recharging events to identify the plurality of recharge patterns, and wherein the external device detects the at least one improper recharge pattern, the method further comprising, prior to receiving the action request:

in response to detection of the at least one improper recharge pattern, transmitting, by at least one of the external device or the implantable medical device, the power source usage information to the remote networking device via the network.

6. The method of claim 1, further comprising, prior to analyzing the plurality of previous recharging events to identify the plurality of recharge patterns:

transmitting, by at least one of the external device or the implantable medical device, the power source usage information to the remote networking device via the network, wherein the remote networking device analyzes the plurality of previous recharging events to identify the plurality of recharge patterns of the plurality of previous recharging events, and wherein the remote networking device detects the at least one improper recharge pattern of the plurality of recharge patterns based on at least some previous recharging events of the plurality of previous recharging events.

7. The method of claim 6, wherein the power source usage information is transmitted to the remote networking device by at least one of the external device or the implantable medical device at a predetermined time, according to scheduled intervals, or after a recharging event.

8. A device comprising:

a processor configured to:

generate power source usage information related to recharging of a rechargeable power source within an implantable medical device, wherein the power source usage information describes a plurality of previous recharging events of the rechargeable power source;

analyze the plurality of previous recharging events to identify a plurality of recharge patterns of the plurality of previous recharging events; and detect at least one improper recharge pattern of the plurality of recharge patterns based on at least some previous recharging events of the plurality of previous recharging events, wherein the at least one improper recharge pattern comprises at least one of infrequent recharging events, frequent short recharging events, a long period between recharging events, or a low degree of coupling between primary and secondary coils during transcutaneous energy transfer to the rechargeable power source; and a communication circuit configured to:

transmit, in response to the detection of the at least one improper recharge pattern, the power source usage information to a remote networking device via a network; and receive an action request from the remote networking device via the network in response to transmission of the power source usage information.

9. The device of claim 8, wherein the device comprises the implantable medical device.

10. The device of claim 8, wherein the device comprises an external device configured to at least one of communicate with or recharge an implantable medical device.

11. The device of claim 8, wherein the action request comprises a patient instruction regarding a power source recharging technique.

12. A method comprising:

receiving, at a remote networking device via a network, power source usage information related to recharging of a rechargeable power source within an implantable medical device, wherein the power source usage information describes a plurality of previous recharging events of the rechargeable power source;

generating, by the remote networking device, an action request based upon identification of a plurality of recharge patterns in the plurality of previous recharging events and detection of at least one improper recharge pattern of the plurality of recharge patterns based on at least some previous recharging events, wherein the at least one improper recharge pattern comprises at least one of infrequent recharging events, frequent short recharging events, a long period between recharging events, or a low degree of coupling between primary and secondary coils during transcutaneous energy transfer to the rechargeable power source; and transmitting, via the network, the action request from the remote networking device to at least one of an external device or the implantable medical device.

13. The method of claim 12, further comprising presenting the power source usage information to a user in conjunction with therapy parameters that were used by the implantable medical device to deliver therapy when the power source usage information was generated.

14. The method of claim 12, wherein the action request comprises a command that unlocks the power source for use from a disabled state due to an overdischarged battery.

15. The method of claim 12, wherein the action request comprises a patient instruction regarding a power source recharging technique.

16. The method of claim 12, further comprising:

generating, by the at least one of the external device or the implantable medical device, the power source usage information;

transmitting, by the at least one of the external device or the implantable medical device, the power source usage information to the remote networking device via the network; and receiving, by the at least one of the external device or the implantable medical device, the action request from the remote networking device via the network in response to transmission of the power source usage information.

17. The method of claim 12, further comprising, after receiving the power source usage information and before generating the action request:

analyzing, by the remote networking device, the plurality of previous recharging events described by the power source usage information to identify the plurality of recharge patterns of the plurality of previous recharging events; and detecting, by the remote networking device, at least one improper recharge pattern of the plurality of recharge patterns based on at least some previous recharging events of the plurality of previous recharging events,
wherein the at least one improper recharge pattern comprises at least one of infrequent recharging events, frequent short recharging events, the long period between recharging events, or the low degree of coupling between primary and secondary coils during transcutaneous energy transfer to the rechargeable power source.

18. A system comprising:
a remote networking device comprising:
   a communication circuit configured to receive, via a network, power source usage information related to recharging of a rechargeable power source within an implantable medical device, wherein the power source usage information describes a plurality of previous recharging events of the rechargeable power source; and
   a processor configured to:
      generate an action request based upon identification of a plurality of recharge patterns in the plurality of previous recharging events and detection of at least one improper recharge pattern of the plurality of recharge patterns based on at least some previous recharging events of the plurality of previous recharging events, wherein the at least one improper recharge pattern comprises at least one of infrequent recharging events, frequent short recharging events, a long period between recharging events, or a low degree of coupling between primary and secondary coils during transcutaneous energy transfer to the rechargeable power source; and
      control the communication circuit to transmit, via the network, the action request from the remote networking device to at least one of an external device or the implantable medical device.

19. The system of claim 18, wherein the remote networking device further comprises a user interface, wherein the processor of the remote networking device is configured to present, via the user interface, the power source usage information to a user in conjunction with therapy parameters that were used by the implantable medical device to deliver therapy when the power source usage information was generated.

20. The system of claim 18, wherein the action request comprises a patient instruction regarding a power source recharging technique.

21. The system of claim 18, wherein the at least one of the external device or the implantable medical device comprises:
   a processor configured to generate the power source usage information; and
   a communication circuit configured to transmit the power source usage information to the remote networking device via the network and receive the action request from the remote networking device via the network in response to transmission of the power source usage information.

22. The system of claim 21, wherein the device comprises the implantable medical device.

23. The system of claim 21, wherein the device comprises the external device, and the external device is configured to at least one of communicate with or recharge the implantable medical device.

24. The system of claim 21, wherein the communication circuit of the at least one of the external device or the implantable medical device is configured to transmit the power source usage information at a predetermined time, according to scheduled intervals, or after a recharging event.

25. The system of claim 18, wherein the processor of the remote networking device is further configured to, prior to generation of the action request:
   analyze the plurality of previous recharging events to identify the plurality of recharge patterns of the plurality of previous recharging events; and
   detect at least one improper recharge pattern of the plurality of recharge patterns based on at least some previous recharging events of the plurality of previous recharging events, wherein the at least one improper recharge pattern comprises at least one of infrequent recharging events, frequent short recharging events, the long period between recharging events, or the low degree of coupling between primary and secondary coils during transcutaneous energy transfer to the rechargeable power source.

26. A system comprising:
a first device configured to:
   generate power source usage information related to recharging of a rechargeable power source within the implantable medical device, wherein the power source usage information describes a plurality of previous recharging events of the rechargeable power source;
   analyze the plurality of previous recharging events to identify a plurality of recharge patterns of the plurality of previous recharging events;
   detect at least one improper recharge pattern of the plurality of recharge patterns based on at least some previous recharging events of the plurality of previous recharging events, wherein the at least one improper recharge pattern comprises at least one of infrequent recharging events, frequent short recharging events, a long period between recharging events, or a low degree of coupling between primary and secondary coils during transcutaneous energy transfer to the power source; and
   transmit, in response to the detection of the at least one improper recharge pattern, the power source usage information via a network; and
a second device configured to:
   receive the power source usage information via the network;
   generate an action request based upon the detection of the at least one improper recharge pattern; and
   transmit the action request to the first device via the network,
   wherein the first device is further configured to receive the action request from the second device via the network in response to transmission of the power usage information.

27. The system of claim 26, wherein:
the first device comprises the implantable medical device, and
the second device comprises a remote networking device.

* * * * *